(12) United States Patent
Shimizu et al.

(10) Patent No.: US 7,897,802 B2
(45) Date of Patent: Mar. 1, 2011

(54) PROCESS FOR PRODUCTION OF SUBSTITUTED CYCLOPENTANONE

(75) Inventors: Katsuya Shimizu, Tokyo (JP); Fumio Matsushita, Tokyo (JP)

(73) Assignee: Asahi Kasei Chemicals Corporation, Chiyoda-Ku (JP)

( * ) Notice: Subject to any disclaimer, the term of this patent is extended or adjusted under 35 U.S.C. 154(b) by 450 days.

(21) Appl. No.: 11/922,674

(22) PCT Filed: Jun. 23, 2006

(86) PCT No.: PCT/JP2006/312605
§ 371 (c)(1), (2), (4) Date: Dec. 21, 2007

(87) PCT Pub. No.: WO2007/004442
PCT Pub. Date: Jan. 11, 2007

(65) Prior Publication Data
US 2009/0036692 A1    Feb. 5, 2009

(30) Foreign Application Priority Data

| Jun. 30, 2005 | (JP) | ............................. 2005-191368 |
| Aug. 11, 2005 | (JP) | ............................. 2005-232933 |
| Aug. 29, 2005 | (JP) | ............................. 2005-247039 |
| Nov. 7, 2005 | (JP) | ............................. 2005-321789 |

(51) Int. Cl.
*C07C 69/74* (2006.01)
*C07C 69/66* (2006.01)
*C07C 45/00* (2006.01)

(52) U.S. Cl. .................. 560/122; 560/174; 568/347; 568/379

(58) Field of Classification Search .................. 560/122, 560/174; 568/347, 379
See application file for complete search history.

(56) References Cited

U.S. PATENT DOCUMENTS

| 3,978,108 A | 8/1976 | Teisseire et al. |
| 5,420,306 A | 5/1995 | Noyori et al. |
| 5,874,600 A * | 2/1999 | Rautenstrauch et al. ..... 556/136 |
| 6,586,620 B1 | 7/2003 | Crawford et al. |

FOREIGN PATENT DOCUMENTS

| CN | 1201027 | 12/1998 |
| JP | 45-24771 | 8/1970 |
| JP | 49-75555 | 7/1974 |
| JP | 54-90155 | 7/1979 |
| JP | 62-87555 | 4/1987 |
| JP | 4-54177 | 2/1992 |
| JP | 2002-69477 | 3/2002 |

OTHER PUBLICATIONS

Blaser et al. Journal of Molecular Catalysis A: Chemical 173 (2001), 3-18.*
Ward et al. Tetrahedron 53 (24), 8181-8494, p. 8182, Scheme-1, Year 1994.*
L. Meier et al., "Reaction of Carboxonium Ions of Cyclic Acetals, IX[1).—Synthesis of Rosefuran and Structurally Related Terpene-like Esters, Alcohols, and Olefins" Leibigs Annalen Der Chemie, Issue 4, 1986; pp. 731-740.
J.L. Ward et al., "Molecular Modelling, Synthesis and Biological Activity of Methyl 3-Methyljasmonate and Related Derivatives", Tetrahedron, vol. 53, No. 24, 1997; pp. 8181-8194.
M.F. Schneider et al. "Rhenium and Ruthenium Induced Ring Closing Olefin Metathesis to Hydroazulenes", Tetrahedron, vol. 51, No. 47, 1995; pp. 13003-13014.
Office Action issued Jul. 11, 2008 in corresponding Taiwanese Patent Application No. 095123464.

(Continued)

*Primary Examiner*—Nizal S Chandrakumar
(74) *Attorney, Agent, or Firm*—Staas & Halsey LLP

(57) ABSTRACT

A substituted cyclopentanone represented by the following formula (2):

[Formula 2]

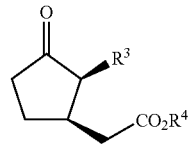

(2)

(wherein $R^3$ and $R^4$ represent a substituent having 1 to 8 carbon atoms, may be the same as $R^1$ and $R^2$, respectively, and may be the same as each other) can be produced by hydrogenating the double bond in a compound represented by the following formula (1):

[Formula 1]

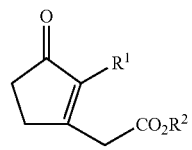

(1)

(wherein $R^1$ and $R^2$ represent a substituent having 1 to 8 carbon atoms) in the presence of a transition metal catalyst by using a carboxylic acid or a specific concentration of a carboxylic acid ester as a solvent. This process can produce a substituted cyclopentanone which is useful as a jasmine fragrance, an intermediate thereof or the like, in a simple and inexpensive manner at a high cis-isomer ratio.

6 Claims, 1 Drawing Sheet

OTHER PUBLICATIONS

English Language Abstract of JP 10-513402 published Dec. 22, 1998.
Motoichi Indo, "Synthetic Perfumes", The Chemical Daily Co. Ltd., pp. 675-678, Mar. 6, 1996.
The Chemical Society of Japan, "Molecular Recognition of Taste and Odor", No. 40, 1999, pp. 166-168.
Schick et al., "Syntheses and Reactions of 2-Alkyl-1,3-cyclopentanediones (2-Alkyl-3-hydroxy-2-cyclopenten-1-ones)", Jul. 1989, p. 479.
Zhou Jingyao et al., "A Convenient Approach to the Synthesis of Methyl Dihydrojasmonate", 1985, p. 491.
Kentaro Hiraga, "Syntheses of 1,3-Cyclopentanediones", Chem. Pharm. Bull. 13, 1965, p. 1359.
J. Šraga et al. "Intramolecular Claisen Condensation of Keto Esters Catalysed by Potassium Triphenylmethoxide" Collect. Czech. Chem. Commun. 42, 1977, p. 998.
I. Mester et al., "Acid Catalyzed Reactions of Alkyl-Furyl Carbinols", Studio Universitatis Babes-Bolyai, Chemia. 19(2), 1974, p. 26.
G. Büchi et al., "An Efficient Synthesis of cis-Jasmone", J. Org. Chem. 31, 1966, p. 977.
International Search Report issued in International Application No. PCT/JP2006/312605, mailed on Sep. 19, 2006.
Tatsuya Shono et al., "Electroreductive Intramolecular Coupling of γ- and δ- Cyanoketones," Tetrahedron Letters, vol. 31, No. 9, 1990, pp. 1303-1306.
European Search Report for European Application No. 06780642.2, mailed on Jul. 15, 2010.

* cited by examiner

[Figure 1]
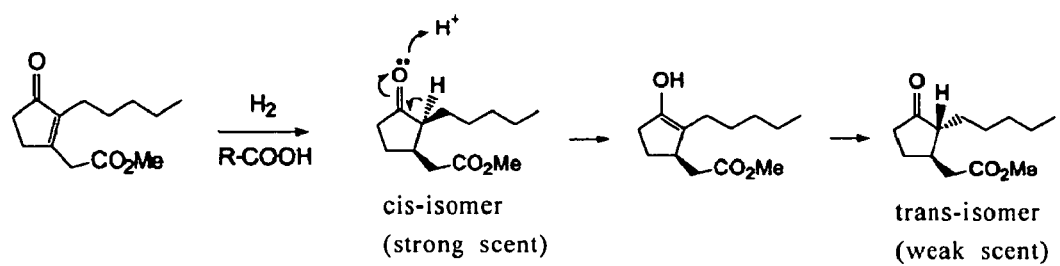

US 7,897,802 B2

PROCESS FOR PRODUCTION OF SUBSTITUTED CYCLOPENTANONE

This application claims the benefit under 35 U.S.C. Section 371, of PCT International Application Number PCT/JP2006/312605, filed Jun. 23, 2006 and Japanese Application No. 2005-191368 filed Jun. 30, 2005 in Japan, Japanese Application No. 2005-232933 filed Aug. 11, 2005 in Japan, Japanese Application No. 2005-247039 filed Aug. 29, 2005 in Japan, Japanese Application No. 2005-321789 file Nov. 7, 2005 in Japan, the contents of which are incorporated herein by reference.

TECHNICAL FIELD

The present invention relates to a process for producing a cis-2,3-disubstituted cyclopentanone useful as a jasmine fragrance, an intermediate thereof or the like, and to an intermediate useful for producing the substituted cyclopentanone and a process for producing the intermediate.

BACKGROUND ART

A 2,3-disubstituted cyclopentanone is an important compound for the synthesis of useful chemical substances such as a jasmine fragrance and prostaglandins. Among others, those having an alkoxycarbonylmethyl group at the 3-position are important for the synthesis of a jasmine fragrance, and many production processes have been disclosed so far.

For example, there are disclosed a process using cyclopentanone as a raw material (Non-patent Document 1) and a process using adipic acid as a raw material (Non-patent Document 2). These processes provide a thermodynamically stable stereoisomer, that is, a trans-2,3-disubstituted cyclopentanone in which substituents at the 2,3-positions are in the trans relationship with each other with respect to the five-membered ring. The percentage of the cis-isomer is generally only 10% or less. However, as a result of recent studies, it has been found that, in a jasmonate which occupies an important position in a jasmine fragrance, a cis-2,3-disubstituted cyclopentanone has a considerably stronger scent than a trans-2,3-disubstituted cyclopentanone (Non-patent Document 3). Thus, development of industrial processes for producing a cis-2,3-disubstituted cyclopentanone is strongly desired. However, as described above, many of conventional techniques provide a trans-2,3-disubstituted cyclopentanone as a main component.

As a technique to compensate for such a difficulty, there is disclosed a process for producing a cis-2,3-disubstituted cyclopentanone by using a catalyst to isomerize the resulting trans-2,3-disubstituted cyclopentanone (patent Document 1). However, in the case of this technique, not only a special apparatus and a special step are required for isomerization, but also a high temperature of 160 to 190° C. is required for isomerization, which inevitably causes thermal degradation. There is a problem that a special apparatus and a special step are further required for removing high boiling impurities produced due to the degradation. In addition, the concentration of the resulting cis-isomer (epimer) is only about 40%.

On the other hand, as a process for selectively synthesizing a cis-2-substituted-3-alkoxycarbonylmethyl cyclopentanone, there is known a process for hydrogenating the double bond in a 2-substituted-3-alkoxycarbonylmethyl cyclopentenone.

Patent Document 2 discloses a process of catalytic hydrogenation in the presence of aluminum alcoholate. The process can provide a desired cis-2-substituted-3-alkoxycarbonylmethyl cyclopentanone at a selectivity of 90% or more. However, in addition to restrictions on reaction operation and equipment that require pressurization of 3 to 10 $kg/cm^2$, it is necessary to use an equivalent amount of aluminum alcoholate as a third component. Moreover, since the aluminum alcoholate added is decomposed by an aqueous acetic acid solution or the like after the reaction, a large amount of aluminum-based wastes are generated, making post-processing difficult. Further, the process also has a difficulty in that the catalyst is polluted with these wastes to make recycling of the catalyst difficult.

Patent Document 3 discloses a process of hydrogenation in the presence of a ruthenium complex having a specific ligand. This document describes that a desired cis-2-substituted-3-alkoxycarbonylmethyl cyclopentanone can be obtained at a high selectivity of 99% or more. However, in addition to the necessity of using a very expensive catalyst of ruthenium, it is necessary to use a special and expensive compound also for the ligand. A complicated pretreatment is also required for the catalyst beforehand. Further, since the process requires a very high hydrogen pressure of 10 to 90 $kg/cm^2$, restrictions on reaction operation and equipment are very large. Furthermore, the technique has a serious difficulty in the industrial implementation thereof in that, since it uses a homogeneous catalyst (dissolved in a solvent), a special operation is required for the separation of the catalyst and the product after reaction. Moreover, in the above technique, since a specific ligand, which is added as a third component, is dissociated from the ruthenium complex based on the dissociation equilibrium, part of the ligand may be transferred to the product. As a result, there was a serious drawback that the composition of a catalyst composition was changed in the catalyst separation operation after reaction and the reproducibility of the catalyst performance was not obtained.

Patent Document 4 discloses a process of hydrogenation in the presence of a rhodium-carbon catalyst in combination with a phosphate or the like. This document describes that a desired cis-2-substituted-3-alkoxycarbonylmethyl cyclopentanone can be obtained at a high selectivity of 90% or more at ordinary pressure. However, according to an experiment by the present inventors, the selectivity of a cis-2-substituted-3-alkoxycarbonylmethyl cyclopentanone showed a very low value of 30% or less. Further, according to the above technique, it is necessary to add a salt such as phosphate as a third component. However, since such a salt has a certain solubility in an organic solvent such as methanol, part of the salt transfers to the product in the catalyst separation operation (filtration of the catalyst) after reaction. As a result, there was a serious drawback that the composition of a catalyst composition was changed and the reproducibility of the catalyst performance was not obtained. As described above, a technique which can selectively synthesize a cis-2-substituted-3-alkoxycarbonylmethyl cyclopentanone and has proved satisfactory in terms of industrial implementation has not yet been reported.

On the other hand, a family of 1,3-cyclopentanediones includes very useful compounds for organic synthesis and useful compounds also as precursors for producing a substituted cyclopentanone according to the present invention. However, they are substances which are far more difficult to synthesize than expected from the apparently simple molecular structure thereof (Non-patent Document 4).

Among others, 1,3-cyclopentanedione itself, which not only has a fundamental structure but also is very useful, is particularly difficult to synthesize. Typical processes for synthesizing 1,3-cyclopentanediones reported so far are illustrated below. A first process is a process for reacting succinic acid with acyl chloride in the presence of aluminum chloride (Non-patent Document 5). According to this process, 1,3-cyclopentanediones can be synthesized in one step, but the yield shows a very low value of 50%. Moreover, according to this process, it is necessary to use a large excess of aluminum chloride and acyl chloride, that is, 2.4 times by mole and 4 times by mole, respectively, relative to the amount of succinic acid as a raw material. This causes production of a large amount of by-product. In addition, it is necessary to use an explosive solvent such as nitrobenzene as a solvent. Thus, it is difficult to consider the above process as a satisfactory process from the standpoint of industrial implementation. Further, since it is known that 1,3-cyclopentanedione which not only has a fundamental structure but also is very useful, cannot be synthesized by the above process (Non-patent Document 4), the above process cannot be a universal process for synthesizing 1,3-cyclopentanediones. A second process is a process for cyclizing a 4-oxoalkanoate with a base. Although this process is also a process in which a 1,3-cyclopentanedione can be synthesized in one step, the yield of 1,3-cyclopentanedione which not only has a fundamental structure but also is very useful, is low. 1,3-cyclopentanedione cannot be produced at all by using a general base (Non-patent Document 6) and can be obtained in at most 60% yield (Non-patent Document 7) only when a special base (potassium triphenylmethoxide) is used. Furthermore, even in the case of a long chain 4-oxoalkanoate which is considered to undergo cyclization relatively easily, the yield is as low as about 35 to 80% (Non-patent Document 4). Thus, it is difficult to consider this technique as a technique that can be industrially implemented. As described above, a technique for producing 1,3-cyclopentanediones which has proved satisfactory in terms of industrial implementation has not yet been reported owing to the difficulty in synthesizing 1,3-cyclopentanediones.

On the other hand, a γ-ketoester is a useful compound for organic synthesis and is also useful as a precursor for producing a substituted cyclopentanone according to the present invention. However, it is difficult to synthesize a γ-ketoester in a small number of steps because it has two types of highly reactive functional groups, that is, ketone and ester in the same molecule. As an example of a few efficient synthetic processes, it is already known that a γ-ketoester can be synthesized at a stroke by treating furfuryl alcohol with hydrogen chloride in an alcohol. For example, Non-patent Document 8 discloses an example of reacting furfuryl alcohol in methanol or ethanol. However, a γ-ketoester can be obtained only in a very low yield of 29 to 36% by this technique. In other words, synthesis of a γ-ketoester with high efficiency has not yet been achieved by conventional techniques.

Further, a substituted cyclopentenone represented by the following formula (15) is a useful compound as a precursor for producing a substituted cyclopentanone according to the present invention. Non-patent Document 5 is known as a process for producing this compound.

[Formula 1]

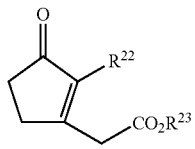

(15)

This production process has a step in which succinic acid is reacted with an acid chloride using aluminum chloride as a catalyst and nitromethane as a solvent. However, this step has a serious problem for the industrial implementation thereof. First, the yield is as low as 50%. In addition, this step requires a large amount of aluminum chloride and an acid chloride, which are difficult in handling due to fuming properties and corrosive properties, that is, 2.4 times by mole and 4 times by mole, respectively, relative to the amount of succinic acid as a raw material. This is not only the problem of production such as a difficulty in operation at the time of charging these compounds and corrosion of reactor materials but also the problem of environmental protection in that a large amount of aluminum-based and chloride-based wastes are discharged after reaction. Moreover, there is also a problem that since nitromethane which is used as a solvent is an explosive substance, a particular safety measure is required for using the same in an industrial scale. As described above, in conventional techniques, there is no process for safely and efficiently producing a substituted cyclopentenone represented by the above formula (15) in an industrial scale.

A 1,3-cyclopentanediones having a structure with a trans-double bond in a side chain, represented by the following formula (17), is a useful compound as an intermediate for producing a substituted cyclopentanone according to the present invention.

[Formula 2]

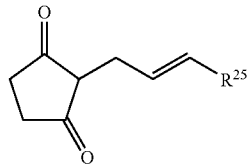

(17)

For synthesizing this compound by conventional techniques, there can be mentioned, for example, a process in which a halide having an allyl group in which the double bond is in trans configuration, represented by the following formula (40):

[Formula 3]

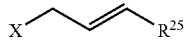

(40)

(wherein $R^{25}$ represents the meaning described below; and X represents a halogen atom) is allowed to react with 1,3-cyclopentanedione in the presence of a base. However, according to this process, it is necessary to stereoselectively synthesize a halide represented by the above formula (40) beforehand. This involved, for example, a problem that a complicated process is required such that the triple bond of a compound represented by the following formula (41):

[Formula 4]

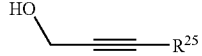

(41)

(wherein $R^{25}$ represents the meaning described below) is hydrogenated with sodium in liquid ammonia, followed by conversion of the alcohol to halogen. In other words, simple production of a 1,3-cyclopentanedione having a trans-double bond in a side chain, represented by the above formula (17), has not yet been achieved by conventional techniques.

If the trans-double bond in the side chain of a compound represented by the following formula (18) could be selectively converted to an oxirane (epoxidation) to synthesize a compound represented by the following formula (19), the double bond in the side chain would be protected. Furthermore, if the oxirane ring could be converted to a diol by its cleavage to the anti-type, the technique may provide a clue to the introduction of a cis-double bond. This could be very useful for the synthesis of a substituted cyclopentanone such as a jasmine fragrance. However, such a technique has not yet been disclosed.

[Formula 5]

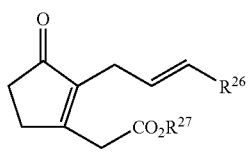

(18)

[Formula 6]

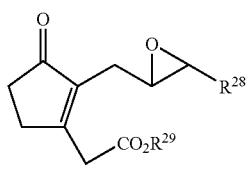

(19)

Methylcyclopentenones such as cis-jasmone and dihydrojasmone occupy an important position among jasmine fragrances, and a large number of production processes have been reported. Many of these processes are based on an intramolecular aldol reaction of a 1,4-diketone. For example, a large number of examples such as Patent Documents 5 and 6 and Non-patent Document 9 are known. According to these processes, specific methylcyclopentenones can be produced. However, since these processes are uniquely specialized in the production of these specific methylcyclopentenones, it is difficult to produce other useful fragrances by using these processes. In the fragrance industry, it is indispensable that many types of fragrance can be produced freely, and a production process specialized in one fragrance material as described above is very inefficient. For example, it is practically impossible to derivatively obtain jasmonates which are especially useful and have a large demand in jasmine fragrance by using these processes, and a totally different production process must be adopted to produce these esters. Therefore, there was a difficulty in that unreasonableness and disadvantageousness arise in supply of production equipment and raw materials and the like. In other words, conventional techniques have not yet achieved derivative production of jasmonates and methylcyclopentenones, both of which occupy important positions in the field of jasmine fragrance, through the same synthetic route.

There are many reports on the production process of γ-lactones, and many of them are on the production of γ-lactones from an alcohol and an acrylic acid derivative by radical addition with an organic peroxide and the like. For example, there is known a process in which an acrylic acid derivative is allowed to react with an alcohol in the presence of di-t-butyl peroxide and zinc halide (Patent Document 7). However, γ-lactones produced by this process generally had a serious drawback in that they had a plastic-like flavor and sourness and their original good fruity or floral fragrance was impaired. Various purification processes to improve such a drawback had been disclosed, but none of them was perfect. Further, there was also a difficulty in that an organic peroxide such as di-t-butyl peroxide was a dangerous substance having explosiveness and required special measures for the handling thereof. Thus, development of a fundamentally different production process of γ-lactones has been strongly desired.

[Patent Document 1] Japanese Patent Laid-Open No. 2002-69477
[Patent Document 2] Japanese Patent Laid-Open No. 54-90155
[Patent Document 3] National Publication of International Patent Application No. 10-513402
[Patent Document 4] Japanese Patent Laid-Open No. 62-87555
[Patent Document 5] Japanese Patent Publication No. 45-24771
[Patent Document 6] Japanese Patent Laid-Open No. 49-75555
[Patent Document 7] Japanese Patent Laid-Open No. 4-54177
[Non-patent Document 1] Motoichi Indo, "Gosei Koryo (Synthetic Perfume)", published by The Chemical Daily Co., Ltd., Mar. 22, 2005, amended and revised edition, p. 677
[Non-patent Document 2] Motoichi Indo, "Gosei Koryo (Synthetic Perfume)", published by The Chemical Daily Co., Ltd., Mar. 22, 2005, amended and revised edition, p. 676
[Non-patent Document 3] Edited by The Chemical Society of Japan, "Aji-to Nioi-no Bunshi Ninshiki (Molecular Recognition of Taste and Odor)", published by Japan Scientific Societies Press, Apr. 10, 2000, p. 168
[Non-patent Document 4] Synthesis, 479 (1989)
[Non-patent Document 5] Zhou Jingyao, Lin Guomei Sun Wei Sun Jing, "Youji Huaxue", 1985, No. 6, p. 491
[Non-patent Document 6] Chem. Pharm. Bull. 13, 1359 (1965)
[Non-patent Document 7] Collect. Czech. Chem. Commun. 42, 998 (1977)
[Non-patent Document 8] Studia Universitatis Babes-Bolyai, Chemia, 19 (2), 26 (1974)
[Non-patent Document 9] J. Org. Chem., 31, 977 (1966)

DISCLOSURE OF THE INVENTION

Problems to be Solved by the Invention

An object of the present invention is to provide a process for producing a cis-2,3-disubstituted cyclopentanone highly stereoselectively and industrially advantageously that is useful as a jasmine fragrance, an intermediate thereof or the like, and to provide a useful intermediate for producing the substituted cyclopentanone and a process for producing the intermediate in an industrially advantageous manner.

DISCLOSURE OF THE INVENTION

The present inventors have completed the present invention as a result of intensive studies for solving the above problems. The present invention will be described below:

<1> A process for producing a substituted cyclopentanone represented by the formula (2):

[Formula 8]

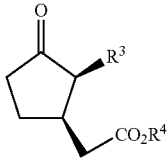

(2)

(wherein $R^3$ and $R^4$ represent a substituent having 1 to 8 carbon atoms, may be the same as $R^1$ and $R^2$, respectively, and may be the same as each other) characterized by hydrogenating the double bond in the five-membered ring of a compound represented by the formula (1):

[Formula 7]

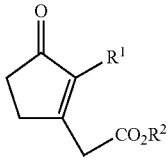

(1)

(wherein $R^1$ and $R^2$ represent a substituent having 1 to 8 carbon atoms and may be the same as each other) in the presence of a transition metal catalyst by using a carboxylic acid as a solvent.

<2> The process for producing a substituted cyclopentanone according to the above 1, characterized in that the carboxylic acid is lactic acid.

<3> The process for producing a substituted cyclopentanone according to the above 1 or 2, characterized in that a third component soluble in the solvent and affecting catalyst activity is not added.

<4> The process for producing a substituted cyclopentanone according to the above 1 or 2, characterized in that the concentration of the carboxylic acid in the reaction solution at the start of hydrogenation is from 0.05 part by weight to 1,000 parts by weight based on one part by weight of the compound represented by the above formula (1).

<5> The process for producing a substituted cyclopentanone according to the above 1 or 2, characterized in that the transition metal is palladium.

<6> The process for producing a substituted cyclopentanone according to the above 1 or 2, characterized in that the transition metal catalyst is palladium-carbon.

<7> A process for producing a substituted cyclopentanone represented by the formula (2):

[Formula 10]

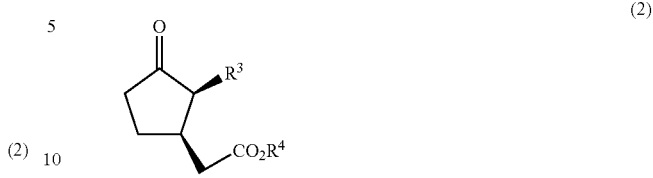

(wherein $R^3$ and $R^4$ represent a substituent having 1 to 8 carbon atoms, may be the same as $R^1$ and $R^2$, respectively, and may be the same as each other) characterized by hydrogenating the double bond in the five-membered ring of a compound represented by the formula (1):

[Formula 9]

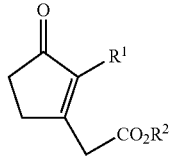

(1)

(wherein $R^1$ and $R^2$ represent a substituent having 1 to 8 carbon atoms and may be the same as each other) in the presence of a transition metal catalyst by using a carboxylic acid ester as a solvent, wherein the concentration of the carboxylic acid ester in the reaction solution at the start of hydrogenation is from 0.05 part by weight to 1,000 parts by weight based on one part by weight of the compound represented by the above formula (1).

<8> The process for producing a substituted cyclopentanone according to the above 7, characterized in that a third component soluble in the solvent and affecting catalyst activity is not added.

<9> The process for producing a substituted cyclopentanone according to the above 7 or 8, characterized in that the transition metal is palladium.

<10> The process for producing a substituted cyclopentanone according to the above 7 or 8, characterized in that the transition metal catalyst is palladium-carbon.

<11> A process for producing a 1,3-cyclopentanedione represented by the following formula (4):

[Formula 12]

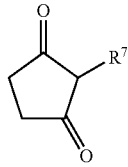

(4)

(wherein $R^7$ represents a hydrogen atom or a substituent having 1 to 8 carbon atoms and may be the same as $R^5$) characterized by adding a base to a compound represented by the following formula (3):

[Formula 11]

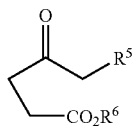

(3)

(wherein $R^5$ represents a hydrogen atom or a substituent having 1 to 8 carbon atoms; $R^6$ represents a substituent having 1 to 8 carbon atoms; and $R^5$ and $R^6$ may be the same as each other) and heating the resulting mixture in a solvent containing aprotic polar solvent in an amount of 10 wt % or more and 100 wt % or less to thereby cyclize the compound represented by the formula (3).

<12> The process for producing a 1,3-cyclopentanedione according to the above 11, characterized in that the aprotic polar solvent is dimethyl sulfoxide.

<13> The process for producing a 1,3-cyclopentanedione according to the above 11 or 12, characterized by carrying out the cyclization while distilling off the solvent under reduced pressure.

<14> A process for producing a γ-ketoester represented by the following formula (7):

[Formula 15]

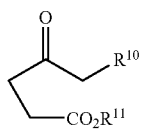

(7)

(wherein $R^{10}$ represents a hydrogen atom or a substituent having 1 to 8 carbon atoms;

$R^{11}$ represents a substituent having 1 to 8 carbon atoms; $R^{11}$ may be the same as $R^8$;

$R^{11}$ may be the same as $R^9$; and $R^{10}$ and $R^{11}$ may be the same as each other) characterized by cleaving a furfuryl alcohol represented by the following formula (5):

[Formula 13]

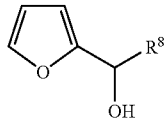

(5)

(wherein $R^8$ represents a hydrogen atom or a substituent having 1 to 8 carbon atoms) with hydrogen chloride in the presence of an alcohol represented by the following formula (6):

[Formula 14]

(6)

(wherein $R^9$ represents a hydrocarbon group having 3 or more carbon atoms).

<15> A process for producing a substituted cyclopentenone characterized by comprising the following 6 steps:

(the first step) a step of cleaving a furfuryl alcohol represented by the following formula (8):

[Formula 16]

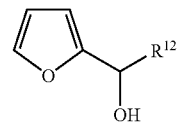

(8)

(wherein $R^{12}$ represents a hydrogen atom or a substituent having 1 to 8 carbon atoms) with hydrogen chloride in the presence of an alcohol represented by the following formula (9):

[Formula 17]

$R^{13}OH$ (9)

(wherein $R^{13}$ represents a hydrocarbon group having one or more carbon atoms) to produce a γ-ketoester represented by the following formula (10):

[Formula 18]

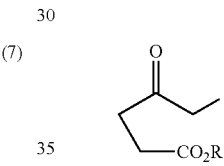

(10)

(wherein $R^{14}$ represents a hydrogen atom or a substituent having 1 to 8 carbon atoms;

$R^{15}$ represents a substituent having 1 to 8 carbon atoms; $R^{14}$ may be the same as $R^{12}$;

$R^{15}$ may be the same as $R^{13}$; and $R^{14}$ and $R^{15}$ may be the same as each other);

(the second step) a step of hydrolyzing the ester group in the γ-ketoester represented by the above formula (10) to produce a γ-ketocarboxylic acid represented by the following formula (11):

[Formula 19]

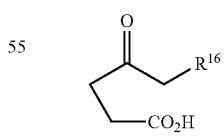

(11)

(wherein $R^{16}$ represents a hydrogen atom or a substituent having 1 to 8 carbon atoms and may be the same as $R^{14}$) and removing by-products;

(the third step) a step of esterifying the carboxylic acid represented by the above (11) to produce a γ-ketoester represented by the following formula (12):

[Formula 20]

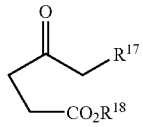
(12)

(wherein $R^{17}$ represents a hydrogen atom or a substituent having 1 to 8 carbon atoms and may be the same as $R^{16}$; $R^{18}$ represents a substituent having 1 to 8 carbon atoms and may be the same as $R^{15}$; and $R^{17}$ and $R^{18}$ may be the same as each other);

(the fourth step) a step of cyclizing the γ-ketoester represented by the above formula (12) to produce a compound represented by the following formula (13):

[Formula 21]

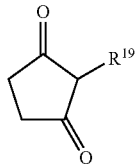
(13)

(wherein $R^{19}$ represents a hydrogen atom or a substituent having 1 to 8 carbon atoms and may be the same as $R^{17}$);

(the fifth step) a step of etherifying the compound represented by the above formula (13) to produce a compound represented by the following formula (14):

[Formula 22]

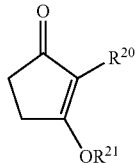
(14)

(wherein $R^{20}$ represents a hydrogen atom or a substituent having 1 to 8 carbon atoms and may be the same as $R^{19}$; $R^{21}$ represents a substituent having 1 to 8 carbon atoms; and $R^{20}$ and $R^{21}$ may be the same as each other); and (the sixth step) a step of adding a malonic ester to the compound represented by the above formula (14) followed by decarboxylation to produce a substituted cyclopentenone represented by the following formula (15):

[Formula 23]

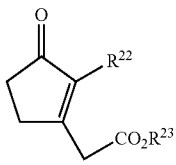
(15)

(wherein $R^{22}$ represents a hydrogen atom or a substituent having 1 to 8 carbon atoms and may be the same as $R^{20}$; $R^{23}$ represents a substituent having 1 to 8 carbon atoms; and $R^{22}$ and $R^{23}$ may be the same as each other).

<16> A process for producing a 1,3-cyclopentanedione represented by the following formula (17):

[Formula 25]

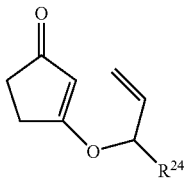
(17)

(wherein $R^{25}$ represents a hydrogen atom or a substituent having 1 to 8 carbon atoms and may be the same as $R^{24}$) characterized by rearranging a compound represented by the following formula (16):

[Formula 24]

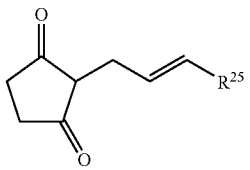
(16)

(wherein $R^{24}$ represents a hydrogen atom or a substituent having 1 to 8 carbon atoms).

<17> A process for producing a substituted cyclopentenone represented by the following formula (19):

[Formula 27]

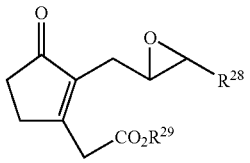
(19)

(wherein $R^{28}$ represents a hydrogen atom or a substituent having 1 to 8 carbon atoms and may be the same as $R^{26}$; $R^{29}$ represents a hydrogen atom or a substituent having 1 to 8 carbon atoms and may be the same as $R^{27}$; and $R^{28}$ and $R^{29}$ may be the same as each other) characterized by selectively oxidizing the double bond in the side chain of a substituted cyclopentenone represented by the following formula (18):

[Formula 26]

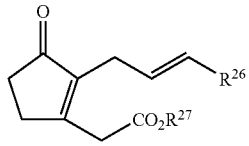

(18)

(wherein $R^{26}$ represents a hydrogen atom or a substituent having 1 to 8 carbon atoms and may be the same as $R^{25}$; $R^{27}$ represents a hydrogen atom or a substituent having 1 to 8 carbon atoms; and $R^{26}$ and $R^{27}$ may be the same as each other).

<18> A process for producing a diol represented by the following formula (20):

[Formula 28]

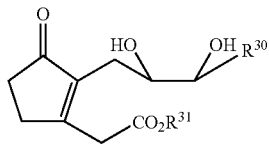

(20)

(wherein $R^{30}$ represents a hydrogen atom or a substituent having 1 to 8 carbon atoms and may be the same as $R^{28}$; $R^{31}$ represents a hydrogen atom or a substituent having 1 to 8 carbon atoms and may be the same as $R^{29}$; and $R^{30}$ and $R^{31}$ may be the same as each other) characterized by hydrolyzing the oxirane ring of a substituted cyclopentenone represented by the above formula (19).

<19> A process for producing a substituted cyclopentenone characterized by comprising the following 9 steps:

(the first step) a step of etherifying 1,3-cyclopentanedione to produce a compound represented by the following formula (21):

[Formula 29]

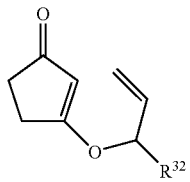

(21)

(wherein $R^{32}$ represents a hydrogen atom or a substituent having 1 to 8 carbon atoms);

(the second step) a step of rearranging the compound represented by the above formula (21) to produce a compound represented by the following formula (22):

[Formula 30]

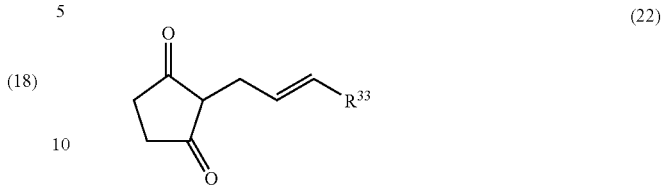

(22)

(wherein $R^{33}$ represents a hydrogen atom or a substituent having 1 to 8 carbon atoms and may be the same as $R^{32}$);

(the third step) a step of etherifying the compound represented by the above formula (22) to produce a compound represented by the following formula (23):

[Formula 31]

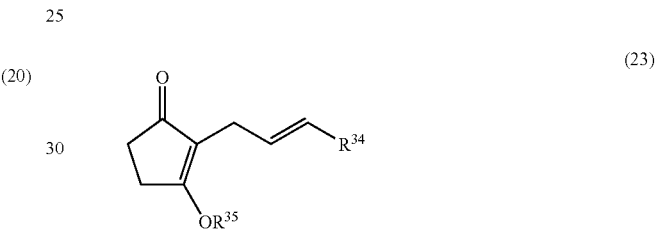

(23)

(wherein $R^{34}$ represents a hydrogen atom or a substituent having 1 to 8 carbon atoms and may be the same as $R^{33}$; $R^{35}$ represents a substituent having 1 to 8 carbon atoms; and $R^{34}$ and $R^{35}$ may be the same as each other);

(the fourth step) a step of adding a malonic ester to the compound represented by the above formula (23) followed by decarboxylation to produce a substituted cyclopentenone represented by the following formula (24):

[Formula 32]

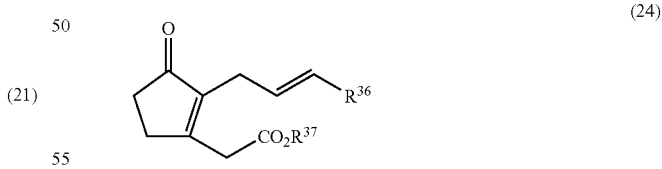

(24)

(wherein $R^{36}$ represents a hydrogen atom or a substituent having 1 to 8 carbon atoms and may be the same as $R^{34}$; $R^{37}$ represents a hydrogen atom or a substituent having 1 to 8 carbon atoms; and $R^{36}$ and $R^{37}$ may be the same as each other);

(the fifth step) a step of selectively oxidizing the double bond in the side chain of the substituted cyclopentenone represented by the above formula (24) to produce a compound represented by the following formula (25):

[Formula 33]

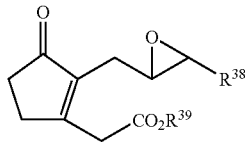

(25)

(wherein $R^{38}$ represents a hydrogen atom or a substituent having 1 to 8 carbon atoms and may be the same as $R^{36}$; $R^{39}$ represents a hydrogen atom or a substituent having 1 to 8 carbon atoms and may be the same as $R^{37}$; and $R^{38}$ and $R^{39}$ may be the same as each other);

(the sixth step) a step of hydrolyzing the oxirane ring of the compound represented by the above formula (25) to produce a diol represented by the following formula (26):

[Formula 34]

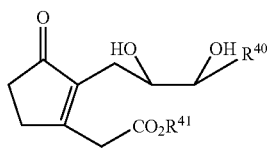

(26)

(wherein $R^{40}$ represents a hydrogen atom or a substituent having 1 to 8 carbon atoms and may be the same as $R^{38}$; $R^{41}$ represents a hydrogen atom or a substituent having 1 to 8 carbon atoms and may be the same as $R^{39}$; and $R^{40}$ and $R^{41}$ may be the same as each other);

(the seventh step) a step of hydrogenating the double bond in the five-membered ring in the above formula (26) to produce a compound represented the following formula (27):

[Formula 35]

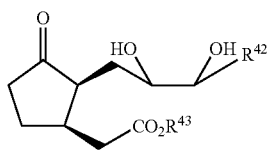

(27)

(wherein $R^{42}$ represents a hydrogen atom or a substituent having 1 to 8 carbon atoms and may be the same as $R^{40}$; $R^{43}$ represents a hydrogen atom or a substituent having 1 to 8 carbon atoms and may be the same as $R^{41}$; and $R^{42}$ and $R^{43}$ may be the same as each other);

(the eighth step) a step of converting the diol represented by the above formula (27) to a dioxolane to produce a compound represented by the following formula (28):

[Formula 36]

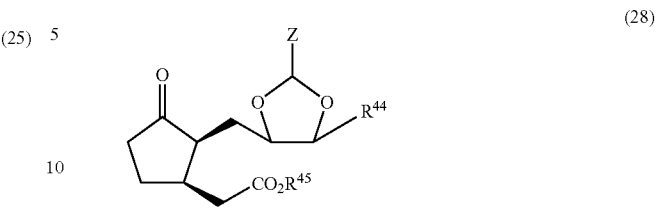

(28)

(wherein $R^{44}$ represents a hydrogen atom or a substituent having 1 to 8 carbon atoms and may be the same as $R^{42}$; $R^{45}$ represents a hydrogen atom or a substituent having 1 to 8 carbon atoms and may be the same as $R^{4}$; $R^{44}$ and $R^{45}$ may be the same as each other; and Z represent an alkoxy group or an amino group having 1 to 6 carbon atoms); and (the ninth step) a step of decomposing the compound represented by the above formula (28) in the presence of a carboxylic acid anhydride to produce a substituted cyclopentanone represented by the following formula (29):

[Formula 37]

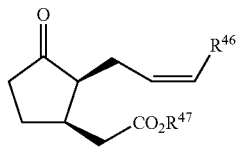

(29)

(wherein $R^{46}$ represents a hydrogen atom or a substituent having 1 to 8 carbon atoms and may be the same as $R^{44}$; $R^{47}$ represents a hydrogen atom or a substituent having 1 to 8 carbon atoms and may be the same as $R^{45}$; and $R^{46}$ and $R^{47}$ may be the same as each other).

<20> A 1,3-cyclopentanedione represented by the above formula (17).

<21> A substituted cyclopentenone represented by the above formula (18).

<22> A substituted cyclopentenone represented by the above formula (19).

<23> A diol represented by the above formula (20).

<24> A compound represented by the above formula (23).

<25> A process for producing a substituted cyclopentenone characterized by comprising the following 3 steps:

(the first step) a step of reacting 1,3-cyclopentanedione with a compound represented by the following formula (30):

[Formula 38]

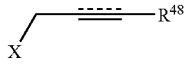

(30)

(wherein $R^{48}$ represents a hydrogen atom or a substituent having 1 to 8 carbon atoms; X represents a leaving group; and the dotted line indicates that a bond may or may not be present) in the presence of a base to produce a compound represented by the following formula (31):

[Formula 39]

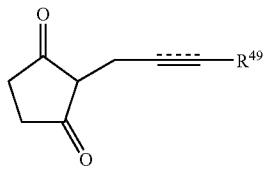
(31)

(wherein $R^{49}$ represents a hydrogen atom or a substituent having 1 to 8 carbon atoms and may be the same as $R^{48}$; and the dotted line represents the above-described meaning);

(the second step) a step of etherifying the compound represented by the above formula (31) to produce a compound represented by the following formula (32):

[Formula 40]

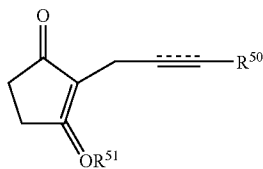
(32)

(wherein $R^{50}$ represents a hydrogen atom or a substituent having 1 to 8 carbon atoms and may be the same as $R^{49}$; $R^{51}$ represents a substituent having 1 to 8 carbon atoms; $R^{50}$ and $R^{51}$ may be the same as each other; and the dotted line represents the above-described meaning);

(the third step) a step of adding a malonic ester to the compound represented by the above formula (32) followed by decarboxylation to produce a compound represented by the following formula (33):

[Formula 41]

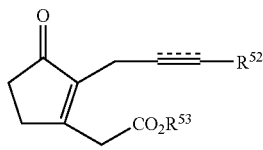
(33)

(wherein $R^{52}$ represents a hydrogen atom or a substituent having 1 to 8 carbon atoms and may be the same as $R^{50}$; $R^{53}$ represents a hydrogen atom or a substituent having 1 to 8 carbon atoms; $R^{52}$ and $R^{53}$ may be the same as each other; and the dotted line represents the above-described meaning).

<26> A process for producing a methylcyclopentenone represented by the following formula (35):

[Formula 43]

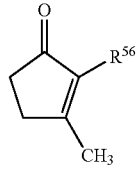
(35)

(wherein $R^{56}$ represents a hydrogen atom or a substituent having 1 to 8 carbon atoms and may be the same as $R^{54}$) characterized by decarboxylating a compound represented by the following formula (34):

[Formula 42]

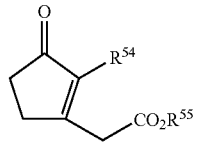
(34)

(wherein $R^{54}$ and $R^{55}$ represent a hydrogen atom or a substituent having 1 to 8 carbon atoms and may be the same as each other).

<27> A process for producing a γ-lactone characterized by comprising the following 2 steps:

(the first step) a step of cleaving a furfuryl alcohol represented by the following formula (36):

[Formula 44]

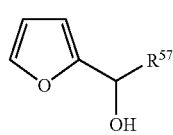
(36)

(wherein $R^{57}$ represents a hydrogen atom or a substituent having 1 to 12 carbon atoms) with hydrogen chloride in the presence of an alcohol represented by the following formula (37):

[Formula 45]

$R^{58}OH$ (37)

(wherein $R^{58}$ represents a hydrocarbon group having one or more carbon atoms) to produce a γ-ketoester represented by the following formula (38):

[Formula 46]

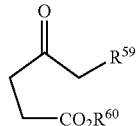
(38)

(wherein $R^{59}$ represents a hydrogen atom or a substituent having 1 to 12 carbon atoms and may be the same as $R^{57}$; $R^{60}$ represents a substituent having 1 to 8 carbon atoms and may be the same as $R^{58}$; and $R^{59}$ and $R^{60}$ may be the same as each other); and (the second step) a step of reducing the γ-ketoester represented by the above formula (38) to produce a γ-lactone represented by the following formula (39):

[Formula 47]

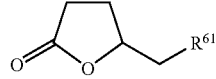

(39)

(wherein $R^{61}$ represents a hydrogen atom or a substituent having 1 to 12 carbon atoms and may be the same as $R^{59}$).

ADVANTAGES OF THE INVENTION

The present invention makes it possible to provide a process for highly stereoselectively and industrially advantageously producing a cis-2,3-disubstituted cyclopentanone useful as a jasmine fragrance, an intermediate thereof or the like. The present invention also makes it possible to industrially advantageously provide a useful intermediate for producing the substituted cyclopentanone.

BEST MODE FOR CARRYING OUT THE INVENTION

The present invention will be specifically described below.

<A First Invention>

A first aspect of the present invention is a process for producing a substituted cyclopentanone represented by the formula (2) by hydrogenating the double bond in a five-membered ring of a substituted cyclopentenone represented by the formula (1) in the presence of a transition metal catalyst by using a carboxylic acid or a specific concentration of a carboxylic acid ester as a solvent.

In the hydrogenation of a compound represented by the above formula (1), it is an essential requirement to use a carboxylic acid and/or a carboxylic acid ester as a solvent to perform hydrogenation. A desired cis-2,3-substituted-alkoxycarbonylmethylcyclopentanone can be obtained with high selectivity by meeting this requirement.

Ketones are known to undergo enolization under acidic conditions (for example, Morrison Boyd "Organic Chemistry" (2nd Volume), 5th Edition, p. 1,139). A 2,3-substituted cyclopentanone is also expected to undergo enolization under acidic conditions. Specifically, it was expected that even if the cis isomer was formed, the configuration on the carbon adjacent to the carbonyl group was inverted, and it isomerized to the thermodynamically stable trans-isomer (FIG. 1). However, as a result of the present inventors' experiment, a surprising fact was found that the selectivity of the cis-isomer was higher in the case where hydrogenation was performed using carboxylic acid as a solvent than the case where a neutral substance such as methanol was used as a solvent. This fact is contrary to the common sense of organic chemistry, and a person skilled in the art cannot predict it easily.

In the above formula (1), $R^1$ and $R^2$ represent a linear or branched alkyl group, alkenyl group, or alkynyl group having 1 to 8 carbon atoms, and these groups may also contain heteroatoms, such as chlorine, bromine, nitrogen, oxygen, sulfur, iron, and cobalt. Specific examples of $R^1$ and $R^2$ include a methyl group, an ethyl group, a butyl group, and a pentyl group, hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. When the application to a jasmine fragrance is taken into consideration, a pentyl group is suitable, and a cis-2-pentenyl group, 2-pentynyl group, a 5-hydroxy-cis-2-pentenyl group, a 5-hydroxy-2-pentynyl group, and the like are also suitable. $R^1$ and $R^2$ may be the same as each other.

In the above formula (2), $R^3$ and $R^4$ represent a linear or branched alkyl group, alkenyl group, or alkynyl group having 1 to 8 carbon atoms, and these groups may also contain heteroatoms, such as chlorine, bromine, nitrogen, oxygen, sulfur, iron, and cobalt. Specific examples of $R^3$ and $R^4$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. When the application to a jasmine fragrance is taken into consideration, a pentyl group is suitable, and a cis-2-pentenyl group, a 2-pentynyl group, a 5-hydroxy-cis-2-pentenyl group, a 5-hydroxy-2-pentynyl group, and the like are also suitable. $R^3$ and $R^4$ may be the same as $R^1$ and $R^2$, respectively, respectively. $R^3$ and $R^4$ may be the same as each other.

A general-purpose carboxylic acid may be used for the above carboxylic acid. Examples of the carboxylic acid include a carboxylic acid which is liquid at ordinary temperatures such as acetic acid, propionic acid, butyric acid, malonic acid, as well as a liquid prepared by mixing a carboxylic acid which is solid at ordinary temperatures such as succinic acid, citric acid, malic acid, lactic acid, and gluconic acid with a liquid such as water. Among others, lactic acid is preferred in that the yield of a compound of the formula (2) is high, and a larger amount of the cis-isomer can be produced.

A general-purpose carboxylic acid ester may be used for the above carboxylic acid ester. Examples of the carboxylic acid ester include a methyl ester, an ethyl ester, a propyl ester, and a butyl ester of the above carboxylic acid. Among others, acetic acid ester is preferred in that the yield of a compound of the formula (2) is high, and a larger amount of the cis-isomer can be produced. Moreover, when a carboxylic acid is compared with a carboxylic acid ester, a carboxylic acid is more preferred because it provides a higher yield of a compound of the formula (2).

A carboxylic acid and/or a carboxylic acid ester only may be used, or a mixed solvent thereof with other solvent(s) (such as alcohols, ethers, and hydrocarbons) may be used, as a solvent for the hydrogenation of the compound of the above formula (1).

In the reaction solution at the start of hydrogenation, the amount of a carboxylic acid and/or a carboxylic acid ester used as a solvent for the hydrogenation of a compound of the above formula (1) is preferably 0.05 parts by weight and less than 1,000 parts by weight, more preferably 0.1 part by weight or more and less than 500 parts by weight, most preferably 1 part by weight or more and less than 200 parts by weight, based on one part by weight of the compound represented by the above formula (1), because the reaction rate and the cis-isomer ratio can be maintained.

A general-purpose transition metal catalyst can be used as the above transition metal catalyst. Examples of a heterogeneous catalyst include palladium, rhodium, ruthenium, Raney, platinum and nickel, including Pd-carbon, Rh-carbon and Ru-carbon as a carbon-loaded catalyst; $Pd-Al_2O_3$, $Rh-Al_2O_3$ and $Ru-Al_2O_3$ as an inorganic substance-loaded catalyst; $PtO_2$ as an oxide-based catalyst; Pt as a metal-based catalyst; Raney Ni as an alloy-based catalyst; and silk-Pd as a protein-loaded catalyst. Further, examples of a homogeneous catalyst include a Wilkinson complex (RhCl $(PPh_3)_3$). A heterogeneous catalyst is preferred in terms of the ease of separation after a reaction, and palladium is most effective of all. Among others, a carbon-loaded catalyst is preferred, most preferably Pd-carbon. Activated carbon is also included in the carbon of a carbon-loaded catalyst. The amount of the catalyst to be used is, for example, preferably from 0.01 to 100 parts by weight based on one part by weight of the compound represented by the formula (1). In the carbon-loaded catalyst and inorganic substance-loaded catalyst of a heterogeneous catalyst, the amount of a transition metal to be deposited is not limited, and it is preferably from 0.1 to 50 wt %, most preferably from 1 to 20 wt %.

Although the aforementioned hydrogenation advances easily by introducing hydrogen into a reaction vessel under ordinary pressure, it is also possible to carry out the hydrogenation, for example, under a pressurization of about 1 to 10 $kg/cm^2$ for the purpose of a further increase in the reaction rate or the like.

The reaction temperature in the aforementioned hydrogenation is not limited, and it is preferably from −30° C. to 100° C., more preferably from −10 to 50° C. from a practical point of view.

In performing the aforementioned hydrogenation, all the essential ingredients other than the compound of the formula (1) which is a substrate are substantially a catalyst, a solvent, and hydrogen, and a third component as conventionally needed in order to affect catalytic activity, specifically, to increase the yield of a compound of the formula (2) or to increase the cis-isomer ratio in the compound of the formula (2) is unnecessary. In particular, it is not necessary to add a third component which is soluble in a solvent. Examples of such a third component include co-catalysts such as an aluminum alcoholate, a phosphate, an acetate, and a bidentate diphosphine ligand. Therefore, a compound of the formula (2) and a catalyst can be separated easily only by filtering out the catalyst after the end of the reaction, and the catalyst can also be reused as it is. This is a great advantage when producing a compound of the formula (2) industrially and is a great progress over prior art. When adding such a third component for another purpose, a very small amount such as from 0.01 to 0.5 time by mole may be added without affecting the reaction system. Note that the above third component does not include a substance which is easily filtered from a compound of the formula (2), a solvent, or a substance which does not substantially affect the isomer ratio or the yield of a compound of the formula (1) or a compound of the formula (2). Such a substance can be added in the range of 0.01 to twice by mole based on the catalyst according to the purpose.

After the completion of hydrogenation reaction, the target compound of the formula (2) can be obtained by filtering a catalyst and purifying the compound by a known process.

<A Second Invention>

A second aspect of the present invention is a process of producing a 1,3-cyclopentanedione by heating a compound of the above formula (3) and a base in an aprotic polar solvent to thereby cyclize the compound. In the aforementioned production process, it is an essential requirement to react a compound of the formula (3) with a basic substance in a solvent containing an aprotic polar solvent in an amount of 10 wt % or more and 100 wt % or less. By satisfying this requirement, a 1,3-cyclopentanedione can be obtained in a high yield.

A 1,3-cyclopentanedione represented by the formula (4) obtained in the present invention can be used also as a precursor for producing the above compound of the formula (2). By satisfying the requirements for the present invention, the 1,3-cyclopentanedione can be obtained in a high yield.

In the above formula (3), $R^5$ represents a hydrogen atom or a linear, branched, or cyclic alkyl group, alkenyl group, or alkynyl group having 1 to 8 carbon atoms. Specific examples of $R^5$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. When the application to a jasmine fragrance is taken into consideration, a pentyl group is suitable, and a cis-2-pentenyl group, a 2-pentynyl group, and the like are also suitable.

In the above formula (3), $R^6$ represents a linear, branched, or cyclic alkyl group, alkenyl group, or alkynyl group having 1 to 8 carbon atoms. Specific examples of $R^6$ include a methyl group, an ethyl group, a butyl group, a pentyl group, and a hexyl group as an alkyl group; a pentenyl group as an alkenyl group; and a pentynyl group as an alkynyl group. An alkyl group is preferred, and a methyl group is most preferred. $R^5$ and $R^6$ may be the same as each other.

In the above formula (4), $R^7$ represents a hydrogen atom or a linear, branched, or cyclic alkyl group, alkenyl group, or alkynyl group having 1 to 8 carbon atoms. Specific examples of $R^7$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. When the application to a jasmine fragrance is taken into consideration, a pentyl group is suitable, and a cis-2-pentenyl group, a 2-pentynyl group, and the like are also suitable. $R^7$ may be the same as $R^5$.

The content of an aprotic polar solvent is still more preferably 20 wt % or more and 100 wt % or less, most preferably 50 wt % or more and 100 wt % or less.

The aforementioned aprotic polar solvent includes dimethyl sulfoxide (DMSO), dimethylformamide (DMF), dimethylacetamide (DMAC), hexamethylphosphoric triamide (HMPT), N-methylpyrrolidone (NMP), etc., and these can be used alone or in combination. The most preferred among these aprotic polar solvents is dimethyl sulfoxide (DMSO) which has high solubility of a base and does not deteriorate easily due to a base.

Components other than an aprotic polar solvent may be contained in the solvent used for the aforementioned production. For example, a hydrocarbon solvent such as toluene and xylene, and an alcoholic solvent such as methanol and ethanol can be used. The range of the content of the components other than an aprotic polar solvent in the solvent is 0 wt % or more and less than 90 wt %, more preferably 0 wt % or more and less than 80%, most preferably 0 wt % or more and less than 50 wt %.

The concentration of the compound represented by the above formula (3) in the reaction solution may be, for example, in the range of 0.01 to 10 mol/L, but a more desirable result will be obtained in many cases when the compound is allowed to react in a relatively diluted system of from 0.01 to 5 mol/L, more preferably from 0.01 to 1 mol/L.

A general-purpose base may be used as the base used in the above production process. For example, it is a metal alkoxide such as sodium methoxide, sodium ethoxide, potassium methoxide, potassium ethoxide, and potassium t-butoxide; a metallic amide such as lithium diisopropylamide and lithium hexamethyldisilazane; and the like. A metal alkoxide is preferred, and sodium methoxide is most preferred. This base is preferably used in an amount of 1.0 mole or more and 10 moles or less, more preferably 1.5 moles or more and 10 moles or less based on the compound of the formula (3).

Although there is no limit to heating temperature, when a practical rate of reaction to be obtained and thermal stability of dimethyl sulfoxide are taken into consideration, it is preferably from 50 to 150° C., most preferably from 60 to 120° C.

In the process of producing 1,3-cyclopentanedione according to the present invention, a more desirable result is obtained in many cases by satisfying the following two requirements.

1. The compound represented by the above formula (3) is added dropwise to a mixture of an aprotic polar solvent and a basic substance. At this time, the compound represented by the above formula (3) diluted with the above-mentioned solvent or other solvents beforehand may be added dropwise. The concentration to which it is diluted is, for example, from 0.01 mol/l to 10 mol/l. Although there is no limit to the drop time, it is preferably from 10 minutes to 5 hours, most preferably from 30 minutes to 3 hours.

2. Cyclization is performed while distilling off a solvent under reduced pressure. Although decompression degree may be suitably set in the range where foaming does not become a problem, it is preferably 300 mmHg or less and 0.1 mmHg or more, more preferably 200 mmHg or less and 0.1 mmHg or more. When foaming is intense at the time of decompression, a defoaming agent may be suitably added.

After the completion of the above reaction, the target compound of the formula (3) can be obtained by performing purification in a known manner.

<A Third Invention>

A third aspect of the present invention is a process for producing a γ-ketoester of the above formula (7) characterized by cleaving a furfuryl alcohol represented by the above formula (5) with hydrogen chloride in the presence of an alcohol represented by the formula (6). Specifically, it can be produced by heating the reaction liquid containing a furfuryl alcohol of the formula (5), an alcohol of the formula (6), and hydrogen chloride. The compound of the formula (7) is useful also as a precursor at the time of producing a substituted cyclopentanone represented by the above formula (2), or a 1,3-cyclopentanedione represented by the above formula (4). By satisfying the requirements for the present invention, 1,3-cyclopentanediones can be obtained in a high yield.

Specifically, in the above formula (5), $R^8$ represents a hydrogen atom or a linear, branched, or cyclic alkyl group, alkenyl group, or alkynyl group having 1 to 8 carbon atoms. Specific examples of $R^8$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. When the application to a jasmine fragrance is taken into consideration, a pentyl group is suitable, and a cis-2-pentenyl group, a 2-pentynyl group, and the like are also suitable.

In the above formula (6), $R^9$ represents a hydrocarbon group having 3 or more carbon atoms. Specific examples of $R^9$ include an n-propyl group, an isopropyl group, an n-butyl group, an isobutyl group, a t-butyl group, an n-pentyl group, an n-hexyl group, an n-heptyl group, an n-octyl group, a cyclohexyl group, and a benzyl group as an alkyl group; an allyl group and a methallyl group as an alkenyl group; and the like. When ease in distilling off, safety, cost, etc. in the treatment after reaction are taken into consideration, an alkyl group is preferred; and among others, an n-propyl group, an isopropyl group, an n-butyl group, an isobutyl group, and a t-butyl group are preferred, most preferably an n-butyl group and an isobutyl group.

In the above formula (7), $R^{10}$ represents a hydrogen atom, or a linear, branched, or cyclic alkyl group, alkenyl group, or alkynyl group having 1 to 8 carbon atoms. Specific examples of $R^{10}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. When the application to a jasmine fragrance is taken into consideration, a pentyl group is suitable, and a cis-2-pentenyl group, a 2-pentynyl group, and the like are also suitable. $R^{10}$ may be the same as $R^8$.

In the above formula (7), $R^{11}$ represents a linear, branched, or cyclic alkyl group, alkenyl group, or alkynyl group having 1 to 8 carbon atoms. Specific examples of $R^{11}$ include a methyl group, an ethyl group, a butyl group, a pentyl group, and a hexyl group as an alkyl group; a pentenyl group as an alkenyl group; and a pentynyl group as an alkynyl group. An alkyl group is preferred, and a methyl group is most preferred. $R^{11}$ may be the same as $R^9$, and $R^{10}$ and $R^{11}$ may be the same as each other.

The alcohol represented by the above formula (6) is preferably used in an equimolar amount or more and in an amount of 100 times by mole or less, more preferably in an amount of 1.5 times by mole or more and 80 times by mole or less, based on a furfuryl alcohol represented by the formula (5).

In the reaction liquid used for the aforementioned production process, although other components, such as methanol, ethanol, ether, tetrahydrofuran, toluene, and xylene, may be present in addition to the alcohol of the formula (6), the percentage may be from about 0.01 wt % to 50 wt % of the reaction liquid.

The process of supplying hydrogen chloride into a reaction liquid includes a process of blowing hydrogen chloride gas; a process of adding hydrochloric acid (an aqueous solution of hydrogen chloride); and a process of adding an acyl chloride compound such as acetyl chloride and allowing it to react with an alcohol of the above formula (6) or the like, thereby generating hydrogen chloride in the reaction system; and the like. Among these, more desirable result is obtained in many cases when the process of blowing hydrogen chloride gas is taken.

Hydrogen chloride is used in an amount of from 0.01 mole to 5 moles based on 1.0 mole of a furfuryl alcohol of the above formula (5), more preferably from 0.01 mole to 2 moles.

The above heating temperature is from 30 to 150° C., more preferably from 40 to 120° C., most preferably from 50 to 100° C., when a practical reaction rate to be obtained is taken into consideration.

Furthermore, when a furfuryl alcohol of the above formula (5) is added dropwise to the mixture of an alcohol of the above formula (6) with hydrogen chloride, a γ-ketoester can be obtained in a high yield in many cases. In this case, a solution prepared by diluting the compound of the above formula (5) with the alcohol of the above formula (6) or other solvents, etc. beforehand may be added dropwise. Concentration of the solution is, for example, from 0.01 mol/l to 10 mol/l. The time of dropwise addition is, but is not limited to, preferably from 10 minutes to 5 hours, most preferably from 30 minutes to 3 hours.

After the completion of the above reaction, the target γ-ketoester of the formula (7) can be obtained by performing purification in a known manner.

<A Fourth Invention>

A fourth aspect of the present invention is a process for producing a substituted cyclopentenone which consists of the following six steps:

[1] the first step: a step of cleaving furfuryl alcohol represented by the above formula (8) with hydrogen chloride in the presence of an alcohol represented by the above formula (9) to produce a γ-ketoester represented by the above formula (10);

[2] the second step: a step of hydrolyzing the ester in a γ-ketoester represented by the above formula (10) to produce a γ-ketocarboxylic acid represented by the above formula (11) and remove a by-product;

[3] the third step: a step of esterifying a carboxylic acid represented by the above (11) to produce a γ-ketoester represented by the above formula (12);

[4] the fourth step: a step of cyclizing a γ-ketoester represented by the above formula (12) to produce a 1,3-cyclopentanedione represented by the above formula (13);

[5] the fifth step: a step of etherifying a 1,3-cyclopentanedione represented by the above formula (13) to produce an enone represented by the above formula (14); and

[6] the sixth step: a step of adding a malonic ester to an enone represented by the above formula (14) followed by decarboxylation to obtain a substituted cyclopentenone represented by the above formula (15).

By satisfying these requirements, the substituted cyclopentenone represented by the above formula (15) can be produced industrially using general-purpose equipment in a small number of steps without discharging harmful waste.

The substituted cyclopentenone represented by the formula (15) is useful also as a precursor for producing the substituted cyclopentanone represented by the above formula (2).

Each step is described below.

[The First Step]

First, a furfuryl alcohol represented by the above formula (8) is cleaved with hydrogen chloride in the presence of an alcohol represented by the above formula (9) to produce a γ-ketoester represented by the above formula (10). Specifically, it can be attained by heating a compound represented by the above formula (8) in the presence of hydrogen chloride and an alcohol represented by the above formula (9). This step may be performed in the same manner as in the above-mentioned third invention.

In the above formula (8), $R^{12}$ represents a hydrogen atom or a linear or cyclic alkyl group, alkenyl group, or alkynyl group having 1 to 8 carbon atoms, and these groups may also contain a heteroatom. Specific examples of $R^{12}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. When the application to a jasmine fragrance is taken into consideration, a pentyl group is suitable, and a cis-2-pentenyl group, 2-pentynyl group, a 5-hydroxy-cis-2-pentenyl group, a 5-hydroxy-2-pentynyl group, and the like are also suitable.

In the above formula (9), $R^{13}$ represents a hydrocarbon group having one or more carbon atoms. Specific examples of $R^{13}$ include a methyl group, an ethyl group, an n-propyl group, an isopropyl group, an n-butyl group, an isobutyl group, a t-butyl group, an n-pentyl group, an n-hexyl group, an n-heptyl group, an n-octyl group, a cyclohexyl group, and a benzyl group as an alkyl group; an allyl group and a methallyl group as an alkenyl group; and the like. When ease in distilling off, safety, cost, etc. in the treatment after reaction are taken into consideration, an alkyl group is preferred; and among others, an n-propyl group, an isopropyl group, an n-butyl group, an isobutyl group, and a t-butyl group are preferred, most preferably an n-butyl group and an isobutyl group.

In the above formula (10), $R^{14}$ represents a hydrogen atom or a linear or cyclic alkyl group, alkenyl group, and alkynyl group having 1 to 8 carbon atoms, and these groups may also contain a heteroatom. Specific examples of $R^{12}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. When the application to a jasmine fragrance is taken into consideration, a pentyl group is suitable, and a cis-2-pentenyl group, 2-pentynyl group, a 5-hydroxy-cis-2-pentenyl group, a 5-hydroxy-2-pentynyl group, and the like are also suitable. $R^{14}$ may be the same as $R^{12}$.

In the above formula (10), $R^{15}$ represents a linear, branched or cyclic alkyl group, alkenyl group, or alkynyl group having 1 to 8 carbon atoms. Specific examples of $R^{15}$ include a methyl group, an ethyl group, an n-propyl group, an isopropyl group, an n-butyl group, an isobutyl group, a t-butyl group, an n-pentyl group, an n-hexyl group, an n-heptyl group, an n-octyl group, a cyclohexyl group, and a benzyl group as an alkyl group; an allyl group and a methallyl group as an alkenyl group. An alkyl group is preferred. Among others, an n-propyl group, an isopropyl group, an n-butyl group, an isobutyl group, and a t-butyl group are preferred. An n-butyl group and an isobutyl group are most preferred. $R^{15}$ may be the same as $R^{13}$, and $R^{14}$ and $R^{15}$ may be the same as each other.

The compound represented by the above formula (8) can be synthesized by a known process. For example, various processes can be mentioned, such as a process in which hydrogen at the 2-position of furan is drawn out with a strong base such as an alkyllithium and an anion formed is added to an aldehyde represented by the following formula (40):

$$R^{12}\text{—CHO} \quad (40)$$

(wherein $R^{12}$ represents the above meaning); and a process in which an organomagnesium compound represented by the following formula (41):

$$R^{12}MgX \quad (41)$$

(wherein $R^{12}$ represents the above meaning; and X represents Cl or Br) or an organolithium compound represented by the following formula (42):

$$R^{12}Li \quad (42)$$

(wherein $R^{12}$ represents the above meaning) is allowed to be added to furfural. A process of using an organomagnesium compound is suitable for its simplicity.

The alcohol represented by the above formula (9) is preferably used in an equimolar amount or more and in an amount of 100 times by mole or less based on a furfuryl alcohol represented by the formula (8), more preferably in an amount of 1.5 times by mole or more and 80 times by mole or less.

The process of supplying hydrogen chloride into a reaction liquid includes, similar to the above third invention, a process of blowing hydrogen chloride gas; a process of adding hydrochloric acid (an aqueous solution of hydrogen chloride); and a process of adding an acyl chloride compound such as acetyl chloride and allowing it to react with an alcohol of the above formula (9) or the like, thereby generating hydrogen chloride in the reaction system. Among these, more desirable result is obtained in many cases when the process of blowing hydrogen chloride gas is taken.

Hydrogen chloride is used in an amount of from 0.01 mole to 5 moles based on 1.0 mole of a furfuryl alcohol of the above formula (8), more preferably from 0.01 mole to 2 moles.

The reaction temperature is preferably from 30 to 150° C., more preferably from 40 to 120° C., most preferably from 50 to 100° C., when a practical reaction rate to be obtained is taken into consideration.

Furthermore, when a furfuryl alcohol of the above formula (8) is added dropwise to the mixture of an alcohol of the above formula (9) with hydrogen chloride, a γ-ketoester can be obtained in a high yield in many cases. In this case, a solution prepared by diluting the compound of the above formula (8) with the alcohol of the above formula (9) or other solvents, etc. beforehand may be dropped. Concentration of the solution is, for example, from 0.01 mol/l to 10 mol/l. The dropping time is, but is not limited to, preferably from 10 minutes to 5 hours, most preferably from 30 minutes to 3 hours.

[The Second Step]

Next, a γ-ketoester represented by the above formula (10) is hydrolyzed to produce a γ-ketocarboxylic acid represented by the above formula (11) and remove a by-product. According to this step, the by-product produced in the cleavage reaction of the first step can be removed simply and efficiently. This process is markedly excellent in both operability and the product yield compared with the usual purification means such as distillation.

In the above formula (11), $R^{16}$ represents a hydrogen atom or a linear or cyclic alkyl group, alkenyl group, or alkynyl group having 1 to 8 carbon atoms, and these groups may also contain a heteroatom. Specific examples of $R^{16}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. When the application to a jasmine fragrance is taken into consideration, a pentyl group is suitable, and a cis-2-pentenyl group, 2-pentynyl group, a 5-hydroxy-cis-2-pentenyl group, a 5-hydroxy-2-pentynyl group, and the like are also suitable. $R^{16}$ may be the same as $R^{14}$.

This step consists of the following three stages. Any stage consists only of easy operation of mixing or phase separation, and all the stages can be performed in the same vessel.

1. A stage in which γ-ketoester represented by the above formula (10) is hydrolyzed by an aqueous solution which contains 1 to 10 times by mole, preferably 1 to 5 times by mole, based on the ketoester, of an alkali metal hydroxide to form an alkali metal salt of corresponding γ-ketocarboxylic acid.

2. A stage in which the hydrolysate is mixed with a non-water soluble organic solvent to extract a by-product into an organic solvent phase, and then the organic solvent layer is removed by phase separation.

3. A stage in which an alkali metal salt of γ-ketocarboxylic acid is neutralized with an acid to form a γ-ketocarboxylic acid of the formula (11).

General-purpose alkali metal hydroxides such as lithium hydroxide, sodium hydroxide, and potassium hydroxide can be used for the alkali metal hydroxide used in the above 1. A known process may be adopted for the hydrolysis condition; for example, what is necessary is just to mix a γ-ketoester with an aqueous solution of alkali metal hydroxide at 10 to 40° C. An aqueous solution of alkali metal hydroxide in the above 1 may contain water-soluble solvents such as methanol and ethanol for the purpose of improving the compatibility of a reactant or the like. In this case, concentration of alkali metal hydroxide in the aqueous solution of the alkali metal hydroxide may be 0.1 to 40% by weight. The content of the water-soluble solvent in the aqueous solution of the alkali metal hydroxide may be 10 to 95% by weight.

Examples of the non-water soluble organic solvent used in the above 2 include hydrocarbon solvents such as pentane, hexane, toluene, xylene; and ether solvents such as diethyl ether. The above non-water soluble organic solvent may be added, for example, in an amount of 1 to 10 parts by weight based on 1 part by weight of γ-ketocarboxylic acid.

General-purpose acids such as hydrochloric acid and sulfuric acid can be used for the acid used in the above 3.

[The Third Step]

Next, a γ-ketocarboxylic acid represented by the above (11) is esterified using a known process to produce a γ-ketoester represented by the above formula (12).

In the above formula (12), $R^{17}$ represents a hydrogen atom or a linear or cyclic alkyl group, alkenyl group, or alkynyl group having 1 to 8 carbon atoms, and these groups may also contain a heteroatom. Specific examples of $R^{17}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. When the application to a jasmine fragrance is taken into consideration, a pentyl group is suitable, and a cis-2-pentenyl group, 2-pentynyl group, a 5-hydroxy-cis-2-pentenyl group, a 5-hydroxy-2-pentynyl group, and the like are also suitable. $R^{17}$ may be the same as $R^{16}$.

In the above formula (12), $R^{18}$ represents a linear, branched or cyclic alkyl group, alkenyl group, or alkynyl group having 1 to 8 carbon atoms. Specific examples of $R^{18}$ include a methyl group, an ethyl group, an n-propyl group, an isopropyl group, an n-butyl group, an isobutyl group, a t-butyl group, an n-pentyl group, an n-hexyl group, an n-heptyl group, an n-octyl group, a cyclohexyl group, and a benzyl group as an alkyl group; an allyl group and a methallyl group as an alkenyl group. An alkyl group is preferred. Among others, an n-propyl group, an isopropyl group, an n-butyl group, an isobutyl group, and a t-butyl group are preferred. An n-butyl group and an isobutyl group are most preferred. $R^{18}$ may be the same as $R^{15}$, and $R^{17}$ and $R^{18}$ may be the same as each other.

Examples of the above process of esterification include 1) a process of heating a mixture of the carboxylic acid, an acid catalyst in an amount of 0.01 to 10 times by mole based on the carboxylic acid, and an alcohol in an amount of 1 to 100 times by mole based on the carboxylic acid at 50 to 120° C.; and 2)

a process of heating the carboxylic acid and an alcohol in an amount of 1 to 10 times by mole based on the carboxylic acid in benzene or toluene in the presence of an acid catalyst in an amount of 0.01 to 10 times by mole based on the carboxylic acid and azeotropically removing the byproduced water.

The acid catalyst used here includes mineral acids such as hydrogen chloride, sulfuric acid, and phosphoric acid; organic acids such as p-toluenesulfonic acid; and metal-based catalysts such as titanium tetrachloride. From a viewpoint of the yield and cost, hydrogen chloride or sulfuric acid is desirable.

[The Fourth Step]

Next, a γ-ketoester represented by the above formula (12) is cyclized to produce a 1,3-cyclopentanedione represented by the above formula (13). Specifically, it can be attained by heating γ-ketoester represented by the above formula (12) in the presence of a base.

In the above formula (13), $R^{19}$ represents a hydrogen atom or a linear, branched or cyclic alkyl group, alkenyl group, or alkynyl group having 1 to 8 carbon atoms. Specific examples of $R^{19}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. When the application to a jasmine fragrance is taken into consideration, a pentyl group is suitable, and a cis-2-pentenyl group, 2-pentynyl group, and the like are also suitable. $R^{19}$ may be the same as $R^{17}$.

Examples of the above base include metal alkoxides such as sodium methoxide, sodium ethoxide, potassium methoxide, potassium ethoxide, and potassium t-butoxide; and metallic amides such as lithium diisopropylamide and lithium hexamethyldisilazane. A metal alkoxide is preferred, and sodium methoxide is most preferred. The base is preferably used, but is not limited to, in an equimolar amount or more and in an amount of 10 times by mole or less based on a ketoester of the formula (12), more preferably in an amount of 1.5 times by mole or more and 10 times by mole or less.

Examples of the above solvent include toluene and xylene as a hydrocarbon solvent; methanol and ethanol as an alcohol solvent; dimethyl sulfoxide (DMSO), dimethylformamide (DMF), dimethylacetamide (DMAC), hexamethylphosphorotriamide (HMPT), and N-methylpyrrolidone (NMP) as an aprotic polar solvent. Among others, an aprotic polar solvent is preferred, and dimethyl sulfoxide (DMSO) is more preferred. These solvents can be used alone or in combination. The amount of the solvent is preferably 0.1 part by weight or more and less than 1,000 parts by weight, most preferably 1 part by weight or more and less than 500 parts by weight, based on 1 part by weight of the ketoester.

The range of the content of components other than the aprotic polar solvent in the solvent is preferably 0% by weight or more and less than 90% by weight, more preferably 0% by weight or more and less than 80%, most preferably 0% by weight or more and less than 50% by weight.

Although the concentration in the reaction solution of the compound represented by the above formula (12) may be, for example, in the range of 0.01 to 10 mol/L, a more desirable result will be obtained in many cases when the compound is allowed to react in a relatively thin system of 0.01 to 5 mol/L. The concentration is more preferably from 0.01 to 1 mol/L.

When it is taken into consideration that a practical reaction rate is obtained, a reaction temperature of 50 to 150° C. is preferred, more preferably 60 to 120° C.

When this fourth step satisfies the following two requirements, a more desirable result is obtained in many cases.

1. The compound represented by the above formula (12) is added dropwise to a mixture of a solvent and a base. At this time, the compound represented by the above formula (12) may be added dropwise in the state where it is diluted with the above-mentioned solvent or other solvents beforehand. Concentration at the dilution is, for example, from 0.01 mol/l to 10 mol/l. Moreover, the time of dropwise addition is, but is not limited to, preferably 10 minutes to 5 hours, most preferably 30 minutes to 3 hours.

2. Cyclization is performed while distilling off a solvent under reduced pressure. At this time, the degree of reduced pressure is not particularly limited and may be appropriately set in the range where foaming does not become a problem. It is preferably 300 mmHg or less and 0.1 mmHg or more, more preferably 200 mmHg or less and 0.1 mmHg or more. Moreover, when foaming is intense, you may add a defoaming agent suitably.

[The Fifth Step]

Then, the 1,3-cyclopentanedione represented by the above formula (13) is etherified to produce an enone represented by the above formula (14).

In the above formula (14), $R^{20}$ represents a hydrogen atom or a linear, branched, or cyclic alkyl group, alkenyl group, or alkynyl group having 1 to 8 carbon atoms. Specific examples of $R^{20}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. When the application to a jasmine fragrance is taken into consideration, a pentyl group is suitable, and a cis-2-pentenyl group, 2-pentynyl group, and the like are also suitable. $R^{20}$ may be the same as $R^{19}$.

In the above formula (14), $R^{21}$ represents a linear, branched or cyclic alkyl group, alkenyl group, or alkynyl group having 1 to 8 carbon atoms. Specific examples of $R^{21}$ include a methyl group, an ethyl group, an n-propyl group, an isopropyl group, an n-butyl group, an isobutyl group, a t-butyl group, an n-pentyl group, an n-hexyl group, an n-heptyl group, an n-octyl group, a cyclohexyl group, and a benzyl group as an alkyl group; an allyl group and a methallyl group as an alkenyl group. An alkyl group is preferred, and most preferred is a methyl group or an ethyl group. $R^{20}$ and $R^{21}$ may be the same as each other.

The process of etherification of the compound represented by the above formula (13) is preferably, but is not limited to, a process of adding an alcohol having a corresponding substituent to a compound of the formula (13) in the presence of an acid catalyst, followed by heating the resulting mixture, in terms of safety and convenience. The acid catalyst includes hydrogen chloride, sulfuric acid, and phosphoric acid as a mineral acid; p-toluenesulfonic acid as an organic acid; and titanium tetrachloride as a metal-based catalyst. Hydrogen chloride or sulfuric acid is preferred in terms of yield and cost. The amount of the acid catalyst is preferably from 0.01 to 10 times by mole based on a compound of the formula (13).

The amount of an alcohol ($R^{21}$—OH) having a corresponding substituent is preferably from 1 to 100 times by mole based on a compound of the formula (13).

The reaction temperature is preferably in the range of from 50° C. to 120° C., more preferably from 50 to 100° C., further preferably from 60° C. to 90° C., in terms of easiness in industrial implementation.

[The Sixth Step]

Furthermore, a malonic ester is added to an enone represented by the above formula (14) followed by decarboxylation to obtain a substituted cyclopentenone represented by the above formula (15).

In the above formula (15), $R^{22}$ represents a hydrogen atom or a linear, branched, or cyclic alkyl group, alkenyl group, or alkynyl group having 1 to 8 carbon atoms. Specific examples of $R^{22}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. When the application to a jasmine fragrance is taken into consideration, a pentyl group is suitable, and a cis-2-pentenyl group, 2-pentynyl group, and the like are also suitable. $R^{22}$ may be the same as $R^{20}$.

In the above formula (15), $R^{23}$ represents a linear, branched or cyclic alkyl group, alkenyl group, or alkynyl group having 1 to 8 carbon atoms. Specific examples of $R^{23}$ include a methyl group, an ethyl group, an n-propyl group, an isopropyl group, an n-butyl group, an isobutyl group, a t-butyl group, an n-pentyl group, an n-hexyl group, an n-heptyl group, an n-octyl group, a cyclohexyl group, and a benzyl group as an alkyl group; an allyl group and a methallyl group as an alkenyl group. An alkyl group is preferred, and most preferred is a methyl group or an ethyl group. $R^{23}$ may be the same as $R^{21}$. $R^{22}$ and $R^{23}$ may be the same as each other.

This step is a reaction starting from the conjugate addition reaction of a malonic ester to an enone of the above formula (14), followed by elimination and decarboxylation of an alkoxy group. This reaction operation may be in accordance with a known process. For example, a simple process comprises allowing an alkoxide of an alkali metal to act on a malonic ester beforehand, drawing out an active hydrogen of the malonic ester to form an anion, and adding a compound of the above formula (14) thereto, followed by heating the resulting mixture.

The amount of the malonic ester is preferably from 1 to 10 times by mole, most preferably from 1 to 5 times by mole, based on the enone of the above formula (14). The amount of the alkali metal alkoxide is preferably from 1 to 5 times by mole, most preferably from 1 to 2 times by mole, based on the malonic ester.

Examples of alkali metal alkoxides include sodium methoxide, sodium ethoxide, potassium methoxide, potassium ethoxide, and potassium t-butoxide. Sodium methoxide is preferred.

The reaction temperature is preferably in the range of from 50° C. to 100° C., more preferably from 60° C. to 90° C., in terms of easiness in industrial implementation.

After the completion of the above reaction, the target compound of the formula (15) can be obtained by purification using a known process.

<A Fifth Invention>

A fifth aspect of the present invention is a process for producing a 1,3-cyclopentanedione represented by the above formula (17) by rearranging a compound represented by the above formula (16). By satisfying this requirement, the compound of the above formula (17) can be produced simply, while controlling the position and configuration of a side chain double bond. A 1,3-cyclopentanedione of the formula (17) is characterized by having a trans-double bond in the side chain, and it is a compound very useful as an intermediate or the like in the synthesis of a useful substituted cyclopentanone of the above formulas (2) such as a jasmine fragrance, and the present invention makes it possible to provide the compound for the first time. In addition, the compound of the formula (17) can also be used as a precursor for the synthesis of prostaglandins and steroids.

In the above formula (16), $R^{24}$ represents a hydrogen atom or a linear or branched alkyl group, alkenyl group, or alkynyl group having 1 to 8 carbon atoms, and these groups may contain heteroatoms such as chlorine, bromine, nitrogen, oxygen, sulfur, iron, and cobalt. Specific examples of $R^{24}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. An alkyl group is preferred, and most preferred is a methyl group or an ethyl group.

In the above formula (17), $R^{25}$ represents a hydrogen atom or a linear or branched alkyl group, alkenyl group, or alkynyl group having 1 to 8 carbon atoms, and these groups may contain heteroatoms such as chlorine, bromine, nitrogen, oxygen, sulfur, iron, and cobalt. Specific examples of $R^{25}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. An alkyl group is preferred, and most preferred is a methyl group or an ethyl group. $R^{25}$ may be the same as $R^{24}$.

There is no limit to a process of rearranging a compound represented by the above formula (16), but for example, it can be attained only by heating the compound of the above formula (16). The compound may be heated in a solvent or without a solvent to 50 to 250° C., preferably 80 to 200° C., most preferably 120 to 160° C. Specific examples of a solvent include toluene and xylene as a hydrocarbon solvent; and collidine as an amine solvent. Xylene is preferred. The amount of a solvent to be used is preferably from 0.1 to 500 parts by weight, most preferably from 1 to 200 parts by weight, based on 1 part by weight of the compound represented by the above formula (16).

After the completion of the above reaction, the target compound of the formula (17) can be obtained by purification using a known process.

<A Sixth Invention>

A sixth aspect of the present invention is a process for producing a substituted cyclopentenone represented by the above formula (19) by selectively oxidizing the double bond in a substituted cyclopentenone represented by the above formula (18). By satisfying this requirement, it becomes possible to produce the substituted cyclopentenone represented by the above formula (19) simply, while maintaining the configuration of the side-chain double bond.

The substituted cyclopentenone of the formula (18) is characterized by having a trans-double bond in the side chain, and the substituted cyclopentenone represented by the formula (19) has an oxirane ring in the side chain as a feature. Both are compounds very useful as an intermediate or the like in the synthesis of a substituted cyclopentanone useful for a jasmine fragrance or the like. The present invention makes it possible to provide these compounds for the first time. In addition, these compounds are also useful as a precursor for the synthesis of, for example, prostaglandin and steroid.

In the above formula (18), $R^{26}$ represents a hydrogen atom or a linear or branched alkyl group, alkenyl group, or alkynyl group having 1 to 8 carbon atoms, and these groups may contain heteroatoms such as chlorine, bromine, nitrogen, oxygen, sulfur, iron, and cobalt. Specific examples of $R^{26}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. An alkyl group is preferred, and most preferred is a methyl group or an ethyl group. $R^{26}$ may be the same as $R^{25}$.

In the above formula (18), $R^{27}$ represents a hydrogen atom or a linear, branched, or cyclic alkyl group, alkenyl group, or alkynyl group having 1 to 8 carbon atoms. Specific examples of $R^{27}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. An alkyl group is preferred, and most preferred is a methyl group or an ethyl group. $R^{26}$ and $R^{27}$ may be the same as each other.

In the above formula (19), $R^{28}$ represents a linear or branched alkyl group, alkenyl group, or alkynyl group having 1 to 8 carbon atoms, and these groups may contain heteroatoms such as chlorine, bromine, nitrogen, oxygen, sulfur, iron, and cobalt. Specific examples of $R^{28}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. An alkyl group is preferred, and most preferred is a methyl group or an ethyl group. $R^{28}$ may be the same as $R^{26}$.

In the above formula (19), $R^{29}$ represents a hydrogen atom or a linear, branched, or cyclic alkyl group, alkenyl group, or alkynyl group having 1 to 8 carbon atoms. Specific examples of $R^{29}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. An alkyl group is preferred, and most preferred is a methyl group or an ethyl group. $R^{29}$ and $R^{27}$ may be the same as each other, and $R^{28}$ and $R^{29}$ may be the same as each other.

Selective oxidation of only the trans-double bond in the side chain of the compound of the above formula (18) can be simply accomplished by using a peroxide. Specific examples of peroxides include performic acid, peracetic acid, perbenzoic acid, and m-chloroperbenzoic acid (m-CPBA) as a peracid; and hydrogen peroxide, tert-butylhydroperoxide, and cumene hydroperoxide as a hydroperoxide. A peracid is preferred, and m-chloroperbenzoic acid (m-CPBA) is most preferred. The amount of a peroxide to be used is preferably from 1 to 10 times by mole, most preferably from 1 to 2 times by mole, based on the substituted cyclopentenone represented by the above formula (18).

A catalyst such as a vanadium-based, molybdenum-based, or manganese-based catalyst may be used as necessary. The amount of the catalyst to be used is preferably from 0.01 to 10 times by mole, most preferably from 0.1 to 5 times by mole, based on the peroxide.

Furthermore, in this oxidation, a solvent can be used as necessary. Examples of the solvent include hexane, toluene, and xylene as a hydrocarbon solvent; and chloroform and dichloromethane as a chlorinated hydrocarbon solvent. A chlorinated hydrocarbon solvent is preferred, and dichloromethane is most preferred. The amount of the solvent to be used is, but is not limited to, preferably 0.1 to 500 parts by weight, most preferably 1 to 200 parts by weight, based on 1 part by weight of the substituted cyclopentenone represented by the above formula (18).

The temperature of this oxidation reaction is preferably from 0 to 50° C., most preferably from 0 to 30° C.

After the completion of the above reaction, the target compound of the formula (19) can be obtained by purification using a known process.

<A Seventh Invention>

A seventh aspect of the present invention is a process for producing a diol represented by the above formula (20) characterized by hydrolyzing the oxirane ring of a substituted cyclopentenone represented by the above formula (19). By satisfying this requirement, it becomes possible to stereoselectively introduce a diol used as a foothold to introduce a cis-double bond into a side chain particularly important in the synthesis of a jasmine fragrance.

The diol represented by the above formula (20) is characterized by having a diol in the side chain, and it can be used as an intermediate in the synthesis of a substituted cyclopentanone useful for a jasmine fragrance or the like. The present invention makes it possible to provide the compound of the formula (20) for the first time.

In the above formula (20), $R^{30}$ represents a linear or branched alkyl group, alkenyl group, or alkynyl group having 1 to 8 carbon atoms, and these groups may contain heteroatoms such as chlorine, bromine, nitrogen, oxygen, sulfur, iron, and cobalt. Specific examples of $R^{30}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. An alkyl group is preferred, and most preferred is a methyl group or an ethyl group. $R^{30}$ may be the same as $R^{28}$.

In the above formula (20), $R^{31}$ represents a hydrogen atom or a linear, branched, or cyclic alkyl group, alkenyl group, or alkynyl group having 1 to 8 carbon atoms. Specific examples of $R^{31}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. An alkyl group is preferred, and most preferred is a methyl group or an ethyl group. $R^{31}$ and $R^{29}$ may be the same as each other, and $R^{30}$ and $R^{31}$ may be the same as each other.

A known process in which an acid catalyst or a base catalyst is used may be adopted for hydrolysis. Specific examples of an acid catalyst include hydrochloric acid, sulfuric acid, and perchloric acid; and specific examples of a base catalyst include sodium hydroxide and potassium hydroxide. An acid catalyst is preferred, and most preferred is perchloric acid. The amount of the catalyst to be used is preferably from 0.01 to 20 times by mole, most preferably from 0.05 to 10 times by mole, based on the substituted cyclopentenone represented by the above formula (19).

When performing the above hydrolysis, a hydrophilic solvent may be contained for the purpose of improving the compatibility of reactants, or the like. Examples of a hydrophilic solvent include methanol, ethanol, n-butanol, and t-butanol as an alcohol solvent; and diethyl ether, tetrahydrofuran, and dioxane as an ether solvent. Among others, t-butanol is preferred as an alcohol solvent, and tetrahydrofuran is preferred as an ether solvent. Most preferred is tetrahydrofuran. A hydrophilic solvent is used preferably in an amount of 0.01 to 20 parts by weight, most preferably in an amount of 0.1 to 10 parts by weight, based on 1 part by weight of water. Moreover, a hydrophilic solvent is used preferably in an amount of 0.1 to 500 parts by weight, more preferably in an amount of 1 to 200 parts by weight, based on 1 part by weight of the substituted cyclopentenone represented by the above formula (19).

The hydrolysis temperature is generally preferably from about 0° C. to 50° C., most preferably from 10 to 40° C.

After the completion of the above reaction, the target compound of the formula (20) can be obtained by purification using a known process.

<An Eighth Invention>

The present invention provides a process for producing a substituted cyclopentanone represented by the above formula (29) characterized by comprising the following 9 steps. By satisfying this requirement, it becomes possible to highly stereoselectively produce the substituted cyclopentanone represented by the above formula (29), using general-purpose equipment. The substituted cyclopentanone of the above formula (29) is one form of a substituted cyclopentanone represented by the above formula (2), and has a structure particularly useful as a jasmine fragrance.

[1] The first step: a step of etherifying 1,3-cyclopentanedione to produce a compound represented by the above formula (21);

[2] The second step: a step of rearranging a compound represented by the above formula (21) to produce a compound represented by the above formula (22);

[3] The third step: a step of etherifying a compound represented by the above formula (22) to produce an enone represented by the above formula (23);

[4] The fourth step: a step of adding a malonic ester to an enone represented by the above formula (23) followed by decarboxylation to produce a substituted cyclopentenone represented by the above formula (24);

[5] The fifth step: a step of selectively oxidizing the double bond in a substituted cyclopentenone represented by the above formula (24) to produce a compound represented by the above formula (25);

[6] The sixth step: a step of hydrolyzing the oxirane ring of a substituted cyclopentenone represented by the above formula (25) to produce a diol represented by the above formula (26);

[7] The seventh step: a step of hydrogenating the double bond in a five-membered ring of the above formula (26) to produce a compound represented by the above formula (27);

[8] The eighth step: a step of converting a diol represented by the above formula (27) to a dioxolane to produce a compound represented by the above formula (28); and

[9] The ninth step: a step of decomposing a compound represented by the above formula (28) in the presence of a carboxylic acid anhydride to produce a substituted cyclopentanone represented by the above formula (29).

Each step is described below.

[The First Step]

First, 1,3-cyclopentanedione is etherified to produce a compound represented by the above formula (21).

In the above formula (21), $R^{32}$ represents a hydrogen atom or a linear or branched alkyl group, alkenyl group, or alkynyl group having 1 to 8 carbon atoms, and these groups may contain heteroatoms such as chlorine, bromine, nitrogen, oxygen, sulfur, iron, and cobalt. Specific examples of $R^{32}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. An alkyl group is preferred, and most preferred is a methyl group or an ethyl group.

The process of etherification may be in accordance with a common process. For example, the process includes a process of heating under reflux an alcohol represented by the following formula (43):

[Formula 48]

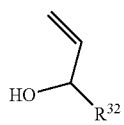

(43)

(wherein $R^{32}$ represents the above meaning) and 1,3-cyclopentanedione in benzene or toluene in the presence of an acid catalyst and azeotropically removing the byproduced water, or a process of reacting an allyl halide represented by the following formula (44):

[Formula 49]

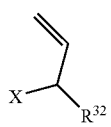

(44)

(wherein $R^{32}$ represents the above meaning; and X represents a halogen atom) with cyclopentanedione in the presence of a base at 50 to 120° C. The former process is preferred.

When the former process is adopted, the amount of the alcohol represented by the above formula (43) is preferably from 1 to 10 times by mole, most preferably from 1.1 to 5 times by mole, based on 1,3-cyclopentanedione. The amount of the acid catalyst used is preferably from 0.01 to 20 times by mole, most preferably from 0.1 to 10 times by mole, based on 1,3-cyclopentanedione. The amount of benzene or toluene used is preferably 0.05 part by weight or more and less than 1,000 parts by weight, based on 1 part by weight of 1,3-cyclopentanedione. It is more preferably 0.1 part by weight or more and less than 500 parts by weight, most preferably 1 part by weight or more and less than 200 parts by weight.

The process of heating under reflux and azeotropically removing the byproduced water may be in accordance with a known process.

On the other hand, when the latter process is adopted, the amount of the allyl halide represented by the above formula (44) is preferably from 1 to 20 times by mole, most preferably from 1.1 to 5 times by mole, based on 1,3-cyclopentanedione. The amount of a base is preferably from 1 to 20 times by mole, most preferably from 1.1 to 10 times by mole, based on 1,3-cyclopentanedione.

[The Second Step]

Next, a compound represented by the above formula (21) is rearranged to produce a compound represented by the above formula (22).

In the above formula (22), $R^{33}$ represents a hydrogen atom or a linear or branched alkyl group, alkenyl group, or alkynyl group having 1 to 8 carbon atoms, and these groups may contain heteroatoms such as chlorine, bromine, nitrogen, oxygen, sulfur, iron, and cobalt. Specific examples of $R^{33}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. An alkyl group is preferred, and most preferred is a methyl group or an ethyl group. $R^{33}$ may be the same as $R^{32}$.

Typically, rearrangement can be accomplished only by heating. For example, the compound may be heated at 50 to 250° C. in a solvent or without a solvent. The heating is preferably at 80 to 200° C., most preferably at 120 to 160° C.

Specific examples of a solvent include toluene and xylene as a hydrocarbon solvent; and collidine as an amine solvent. A hydrocarbon solvent is preferred; and among others, xylene is preferred. The amount of a solvent to be used is preferably from 0.1 to 500 parts by weight, most preferably from 1 to 200 parts by weight, based on 1 part by weight of the compound represented by the above formula (21).

[The Third Step]

Next, a compound represented by the above formula (22) is etherified to produce an enone represented by the above formula (23). The resulting compound of the formula (23) is characterized by having a trans-double bond in the side chain, which is a compound very useful as an intermediate or the like in the synthesis of a substituted cyclopentanone useful for a jasmine fragrance or the like. The present invention makes it possible to provide the compound for the first time.

In the above formula (23), $R^{34}$ represents a hydrogen atom or a linear or branched alkyl group, alkenyl group, or alkynyl group having 1 to 8 carbon atoms, and these groups may contain heteroatoms such as chlorine, bromine, nitrogen, oxygen, sulfur, iron, and cobalt. Specific examples of $R^{34}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. An alkyl group is preferred, and most preferred is a methyl group or an ethyl group. $R^{34}$ may be the same as $R^{33}$.

In the above formula (23), $R^{35}$ represents a linear, branched or cyclic alkyl group, alkenyl group, or alkynyl group having 1 to 8 carbon atoms. Specific examples of $R^{35}$ include a methyl group, an ethyl group, an n-propyl group, an isopropyl group, an n-butyl group, an isobutyl group, a t-butyl group, an n-pentyl group, an n-hexyl group, an n-heptyl group, an n-octyl group, a cyclohexyl group, and a benzyl group as an alkyl group; an allyl group and a methallyl group as an alkenyl group. An alkyl group is preferred, and most preferred is a methyl group or an ethyl group. $R^{34}$ and $R^{35}$ may be the same as each other.

The process of etherification is, but is not limited to, preferably a process of adding an alcohol having a corresponding substituent to a compound of the formula (22) in the presence of an acid catalyst, followed by heating the resulting mixture, in terms of safety and convenience.

Examples of the acid catalyst include hydrogen chloride, sulfuric acid, and phosphoric acid as a mineral acid; p-toluenesulfonic acid as an organic acid; and titanium tetrachloride as a metal-based catalyst. Hydrogen chloride or sulfuric acid is preferred in terms of yield and cost. The amount of the acid catalyst is preferably from 0.01 to 10 times by mole based on a compound of the formula (22).

The amount of an alcohol ($R^{35}$—OH) having a corresponding substituent is preferably from 1 to 100 times by mole based on a compound of the formula (22). The heating temperature is preferably from 50 to 120° C., more preferably from 50 to 100° C., further preferably from 60° C. to 90° C.

[The Fourth Step]

Next, a malonic ester is added to an enone of the above formula (23) followed by decarboxylation to produce a substituted cyclopentenone of the above formula (24). This reaction is a reaction starting from the conjugate addition reaction of a malonic ester to an enone of the above formula (23), followed by elimination reaction of an alkoxy group and decarboxylation reaction.

In the above formula (24), $R^{36}$ represents a hydrogen atom or a linear or branched alkyl group, alkenyl group, or alkynyl group having 1 to 8 carbon atoms, and these groups may contain heteroatoms such as chlorine, bromine, nitrogen, oxygen, sulfur, iron, and cobalt. Specific examples of $R^{36}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. An alkyl group is preferred, and most preferred is a methyl group or an ethyl group. $R^{36}$ may be the same as $R^{34}$.

In the above formula (24), $R^{37}$ represents a hydrogen atom or a linear, branched, or cyclic alkyl group, alkenyl group, or alkynyl group having 1 to 8 carbon atoms. Specific examples of $R^{37}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. An alkyl group is preferred, and most preferred is a methyl group or an ethyl group. $R^{36}$ and $R^{37}$ may be the same as each other.

The operation of this step may be in accordance with a known process. For example, a simple process comprises allowing an alkoxide of an alkali metal to act on a malonic ester beforehand, drawing out an active hydrogen of the malonic ester to from an anion, and adding an enone of the above formula (23) thereto, followed by heating the resulting mixture.

The amount of the malonic ester is preferably from 1 to 10 times by mole, most preferably from 1 to 5 times by mole, based on the enone. The amount of the alkali metal alkoxide is preferably from 1 to 5 times by mole, most preferably from 1 to 2 times by mole, based on the malonic ester. Examples of alkali metal alkoxides include sodium methoxide, sodium ethoxide, potassium methoxide, potassium ethoxide, and potassium t-butoxide. Sodium methoxide is preferred.

The reaction temperature is preferably in the range of from 50° C. to 100° C., more preferably from 60° C. to 90° C., in terms of easiness in industrial implementation.

[The Fifth Step]

Next, a compound represented by the above formula (25) is produced by selectively oxidizing the trans-double bond in a side chain of a substituted cyclopentenone represented by the above formula (24) and introducing an oxirane ring while maintaining the configuration of the side-chain double bond.

In the above formula (25), $R^{38}$ represents a hydrogen atom or a linear or branched alkyl group, alkenyl group, or alkynyl group having 1 to 8 carbon atoms, and these groups may contain heteroatoms such as chlorine, bromine, nitrogen, oxygen, sulfur, iron, and cobalt. Specific examples of $R^{38}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. An alkyl group is preferred, and most preferred is a methyl group or an ethyl group. $R^{38}$ may be the same as $R^{36}$.

In the above formula (25), $R^{39}$ represents a hydrogen atom or a linear, branched, or cyclic alkyl group, alkenyl group, or alkynyl group having 1 to 8 carbon atoms. Specific examples of $R^{39}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. An alkyl group is preferred, and most preferred is a methyl group or an ethyl group. $R^{39}$ and $R^{37}$ may be the same as each other, and $R^{38}$ and $R^{39}$ may be the same as each other.

Selective oxidation of only the trans-double bond in the side chain of the substituted cyclopentenone of the above formula (24) can be simply accomplished, for example, by using a peroxide. Specific examples of peroxides include performic acid, peracetic acid, perbenzoic acid, and m-chloroperbenzoic acid (m-CPBA) as a peracid; and hydrogen peroxide, tert-butylhydroperoxide, and cumene hydroperoxide as a hydroperoxide. A peracid is preferred, and m-chloroperbenzoic acid (m-CPBA) is most preferred. The amount of a peroxide to be used is preferably from 1 to 10 times by mole, most preferably from 1 to 2 times by mole, based on the substituted cyclopentenone represented by the above formula (24).

A catalyst such as a vanadium-based, molybdenum-based, or manganese-based catalyst may be used as necessary. The amount of the catalyst to be used is preferably from 0.01 to 10 times by mole, most preferably from 0.1 to 5 times by mole, based on the peroxide.

In this oxidation, a solvent can be used as necessary. Examples of the solvent include hexane, toluene, and xylene as a hydrocarbon solvent; and chloroform and dichloromethane as a chlorinated hydrocarbon solvent. A chlorinated hydrocarbon solvent is preferred, and dichloromethane is most preferred. The amount of the solvent used is, but is not limited to, preferably 0.1 to 500 parts by weight, most preferably 1 to 200 parts by weight, based on 1 part by weight of the substituted cyclopentenone represented by the above formula (24). The temperature of this oxidation reaction is, but is not limited to, preferably from 0 to 50° C., most preferably from 0 to 30° C.

[The Sixth Step]

Next, a diol represented by the above formula (25) is produced by hydrolyzing the oxirane ring of a substituted cyclopentenone represented by the above formula (26).

In the above formula (26), $R^{40}$ represents a hydrogen atom or a linear or branched alkyl group, alkenyl group, or alkynyl group having 1 to 8 carbon atoms, and these groups may contain heteroatoms such as chlorine, bromine, nitrogen, oxygen, sulfur, iron, and cobalt. Specific examples of $R^{40}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. An alkyl group is preferred, and most preferred is a methyl group or an ethyl group. $R^{40}$ may be the same as $R^{38}$.

In the above formula (26), $R^{41}$ represents a hydrogen atom or a linear, branched, or cyclic alkyl group, alkenyl group, or alkynyl group having 1 to 8 carbon atoms. Specific examples of $R^{41}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. An alkyl group is preferred, and most preferred is a methyl group or an ethyl group. $R^{41}$ may be the same as $R^{39}$, and $R^{40}$ and $R^{41}$ may be the same as each other.

A known process in which an acid catalyst or a base catalyst is used may be adopted for hydrolysis. Specific examples of an acid catalyst include hydrochloric acid, sulfuric acid, and perchloric acid; and specific examples of a base catalyst include sodium hydroxide and potassium hydroxide. Among others, an acid catalyst is preferred, and most preferred is perchloric acid. The amount of the catalyst to be used is, but is not limited to, preferably from 0.01 to 20 times by mole, most preferably from 0.05 to 10 times by mole, based on the substituted cyclopentenone represented by the above formula (25).

In the hydrolysis, a hydrophilic solvent may be contained for the purpose of improving the compatibility of reactants, or the like. Examples of a hydrophilic solvent include methanol, ethanol, n-butanol, and t-butanol as an alcohol solvent; and diethyl ether, tetrahydrofuran, and dioxane as an ether solvent. Among others, t-butanol is preferred as an alcohol solvent, and tetrahydrofuran is preferred as an ether solvent. Most preferred is tetrahydrofuran. The amount of a hydrophilic solvent to be used is preferably from 0.01 to 20 parts by weight, most preferably from 0.1 to 10 parts by weight, based on 1 part by weight of water.

The temperature of the hydrolysis is preferably from about 0 to 50° C., most preferably from 10 to 40° C.

[The Seventh Step]

Furthermore, a compound represented the above formula (27) is produced by hydrogenating the double bond in a five-membered ring represented by the above formula (26).

In the above formula (27), $R^{42}$ represents a hydrogen atom or a linear or branched alkyl group, alkenyl group, or alkynyl group having 1 to 8 carbon atoms, and these groups may contain heteroatoms such as chlorine, bromine, nitrogen, oxygen, sulfur, iron, and cobalt. Specific examples of $R^{42}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. An alkyl group is preferred, and most preferred is a methyl group or an ethyl group. $R^{42}$ may be the same as $R^{40}$.

In the above formula (27), $R^{43}$ represents a hydrogen atom or a linear, branched, or cyclic alkyl group, alkenyl group, or alkynyl group having 1 to 8 carbon atoms. Specific examples of $R^{43}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. An alkyl group is preferred, and most preferred is a methyl group or an ethyl group. $R^{43}$ may be the same as $R^{41}$, and $R^{42}$ and $R^{43}$ may be the same as each other.

A process of hydrogenation includes, for example, a process using a catalyst as an easy example. In the hydrogenation using a catalyst, since hydrogen is generally bonded from the same direction relative to the surface where the double bond is formed, it is possible to selectively synthesize the cis-2,3-disubstituted cyclopentanone targeted by the present invention.

Although a general-purpose catalyst can be used as a catalyst, a transition metal catalyst is preferred because it has high activity. Examples of a heterogeneous catalyst include Pd-carbon, Rh-carbon and Ru-carbon as a carbon-loaded catalyst; Pd—$Al_2O_3$, Rh—$Al_2O_3$ and Ru—$Al_2O_3$ as an inorganic substance-loaded catalyst; $PtO_2$ as an oxide-based catalyst; Pt as a metal-based catalyst; Raney Ni as an alloy-based catalyst; and silk-Pd as a protein-loaded catalyst. Examples of a homogeneous catalyst include a Wilkinson complex (RhCl (PPh$_3$)$_3$). However, a heterogeneous catalyst is preferred in terms of the ease of separation after a reaction, and among others, a carbon-loaded catalyst is preferred, most preferably Pd-carbon. The amount of the catalyst to be used is, for example, preferably from 0.01 to 100 parts by weight based on one part by weight of the compound represented by the formula (26). Note that the carbon in the carbon-loaded catalyst also includes active carbon. In the carbon-loaded catalyst and inorganic substance-loaded catalyst of a heterogeneous catalyst, the amount of a transition metal to be deposited is, but is not limited to, preferably from 0.1 to 50 wt %, most preferably from 1 to 20 wt %.

Although the hydrogenation of a compound represented by the above formula (26) advances easily under ordinary pressure, it is also possible to carry out the hydrogenation, for example, under a pressurization of about 1 to 10 kg/cm$^2$ for the purpose of a further increase in the reaction rate or the like.

The type of a solvent is not limited, and examples of a solvent include methanol, ethanol, propanol, isopropanol, butanol, isobutanol, and t-butanol as an alcohol solvent; diethyl ether, tetrahydrofuran, and dioxane as an ether solvent; benzene, toluene, and xylene as a hydrocarbon solvent; acetic acid, propionic acid, butyric acid, malonic acid, and lactic acid as a carboxylic acid solvent; methyl ester, ethyl ester, propyl ester, and butyl ester of the above carboxylic acid as an ester solvent; acetone and methyl ethyl ketone as a ketone solvent; and water and supercritical $CO_2$ as an inorganic solvent. These can be used alone or in combination. A carboxylic acid solvent or an ester solvent is preferred, and acetic acid or ethyl acetate is most preferred. The amount of a solvent to be used is, but is not limited to, preferably 0.1 part by weight or more and less than 1,000 parts by weight, most preferably 1 part by weight or more and less than 500 parts by weight, based on 1 part by weight of the diol represented by the above formula (26).

The reaction temperature is, but is not limited to, preferably from −30° C. to 100° C., more preferably from −20° C. to 50° C., most preferably from −10 to 50° C., from a practical point of view.

[The Eighth Step]

Then, a compound represented by the above formula (28) is produced by converting a diol represented by the above formula (27) to a dioxolane.

In the above formula (28), $R^{44}$ represents a hydrogen atom or a linear or branched alkyl group, alkenyl group, or alkynyl group having 1 to 8 carbon atoms, and these groups may contain heteroatoms such as chlorine, bromine, nitrogen, oxygen, sulfur, iron, and cobalt. Specific examples of $R^{44}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. An alkyl group is preferred, and most preferred is a methyl group or an ethyl group. $R^{44}$ may be the same as $R^{42}$.

In the above formula (28), $R^{45}$ represents a hydrogen atom or a linear, branched, or cyclic alkyl group, alkenyl group, or alkynyl group having 1 to 8 carbon atoms. Specific examples of $R^{45}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. An alkyl group is preferred, and most preferred is a methyl group or an ethyl group. $R^{45}$ may be the same as $R^{43}$, and $R^{44}$ and $R^{45}$ may be the same as each other.

In the above formula (28), Z represents an alkoxy group or an amino group having 1 to 6 carbon atoms. Specific examples of Z include a methoxy group, an ethoxy group, and a butoxy group as an alkoxy group; and a dimethylamino group, a diethylamino group, and a dibutylamino group as an amino group. An alkoxy group is preferred, and a methoxy group is most preferred.

A process for preparing dioxolane may be in accordance with a known process. Examples of the process include a process in which a diol is allowed to react with an alkyl orthoformate such as methyl orthoformate in the presence of an acid catalyst; and a process in which an N,N-dialkylformamide dialkyl acetal such as N,N-dimethylformamide dimethyl acetal is allowed to react with a diol in the presence of an acid catalyst such as p-toluenesulfonic acid. A process in which a diol is allowed to react with an alkyl orthoformate is preferred, and a process using methyl orthoformate is most preferred. The amount of the alkyl orthoformate is preferably 0.05 part by weight or more and less than 1,000 parts by weight, based on 1 part by weight of the compound represented by the above (27). The amount is more preferably 0.1 part by weight or more and less than 500 parts by weight, most preferably 1 part by weight or more and less than 200 parts by weight.

Examples of the acid catalyst include hydrogen chloride, sulfuric acid, and phosphoric acid as a mineral acid; p-toluenesulfonic acid as an organic acid; and titanium tetrachloride as a metal-based catalyst, and p-toluenesulfonic acid is preferred in terms of yield and cost. The amount of the acid catalyst is preferably from 0.01 to 20 times by mole, most preferably from 0.1 to 10 times by mole, based on a compound represented by the formula (27).

The reaction temperature is, for example, preferably from 20° C. to 150° C., most preferably from 50 to 120° C.

[The Ninth Step]

Finally, a substituted cyclopentanone represented by the above formula (29) is produced by decomposing a compound represented by the above formula (28) in the presence of a carboxylic acid anhydride.

In the above formula (29), $R^{46}$ represents a hydrogen atom or a linear or branched alkyl group, alkenyl group, or alkynyl group having 1 to 8 carbon atoms, and these groups may contain heteroatoms such as chlorine, bromine, nitrogen, oxygen, sulfur, iron, and cobalt. Specific examples of $R^{46}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. An alkyl group is preferred, and most preferred is a methyl group or an ethyl group. $R^{46}$ may be the same as $R^{44}$.

In the above formula (29), $R^{47}$ represents a hydrogen atom or a linear, branched, or cyclic alkyl group, alkenyl group, or alkynyl group having 1 to 8 carbon atoms. Specific examples of $R^{47}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. An alkyl group is preferred, and most preferred is a methyl group or an ethyl group. $R^{47}$ may be the same as $R^{45}$, and $R^{46}$ and $R^{47}$ may be the same as each other.

As the type of the carboxylic acid anhydride, a lower carboxylic acid anhydride is preferred, and most preferred is acetic anhydride. The amount of the carboxylic acid anhydride is, but is not limited to, preferably 0.1 part by weight or more and less than 1,000 parts by weight, most preferably 1 part by weight or more and less than 500 parts by weight, based on 1 part by weight of the compound represented by the above (28).

The decomposition temperature may be in accordance with a known process, and it is preferably from 50 to 200° C., most preferably from 80 to 180° C.

After the completion of the above reaction, the target substituted cyclopentanone of the formula (29) can be obtained by purification using a known process.

<The Ninth Invention>

A ninth aspect of the present invention provides a process for producing a compound represented by the above formula (33) comprising the following 3 steps. By satisfying this requirement, it becomes possible to efficiently produce a compound represented by the above formula (33), using general-purpose equipment. The compound represented by the above formula (33) is also useful as a precursor for producing a substituted cyclopentanone represented by the above formula (2).

[1] The first step: a step of reacting 1,3-cyclopentanedione with a compound represented by the above formula (30) in the presence of a base to produce a compound represented by the above formula (31);

[2] The second step: a step of etherifying a compound represented by the above formula (31) to produce an enone represented by the above formula (32); and

[3] The third step: a step of adding a malonic ester to an enone represented by the above formula (32) followed by decarboxylation to produce a compound represented by the above formula (33).

Each step is described below.

[The First Step]

First, 1,3-cyclopentanedione is reacted with a compound represented by the above formula (30) in the presence of a base.

In the above formula (30), $R^{48}$ represents a hydrogen atom or a linear or branched alkyl group, alkenyl group, or alkynyl group having 1 to 8 carbon atoms, and these groups may contain heteroatoms such as chlorine, bromine, nitrogen, oxygen, sulfur, iron, and cobalt. Specific examples of $R^{48}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. An alkyl group is preferred, and most preferred is a methyl group or an ethyl group. In the above formula (30), X represents a leaving group. There is no limit to the type of a leaving group, and examples thereof include chlorine, bromine, and iodine as a halogen atom, and p-toluene sulfonate group and a methane sulfonate group as a sulfonate group. In the above formula (30), the dotted line indicates that a bond may or may not be present. That is, this bond indicates a triple bond or a double bond.

In the above formula (31), $R^{49}$ represents a hydrogen atom or a linear or branched alkyl group, alkenyl group, or alkynyl group having 1 to 8 carbon atoms, and these groups may contain heteroatoms such as chlorine, bromine, nitrogen, oxygen, sulfur, iron, and cobalt. Specific examples of $R^{49}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. An alkyl group is preferred, and most preferred is a methyl group or an ethyl group. $R^{49}$ may be the same as $R^{48}$. In the above formula (31), the dotted line indicates that a bond may or may not be present. That is, the bond indicates a triple bond or a double bond.

A general-purpose base may be used for a base. Examples of a base include lithium hydroxide, sodium hydroxide, potassium hydroxide, and calcium hydroxide as a metal hydroxide; sodium carbonate, sodium hydrogencarbonate, potassium carbonate, and potassium hydrogencarbonate as a carbonate; sodium methoxide, sodium ethoxide, potassium methoxide, potassium ethoxide, potassium t-butoxide as a metal alkoxide; and lithium diisopropylamide, lithium hexamethyldisilazane as a metallic amide. A metal hydroxide or a carbonate is preferred, and most preferred is potassium hydroxide or potassium carbonate.

The amount of the base to be used is preferably from 1 to 20 times by mole, most preferably from 1 to 5 times by mole, based on 1,3-cyclopentanedione.

The amount of the compound represented by the above formula (30) is preferably from 1 to 20 times by mole, most preferably from 1 to 5 times by mole, based on 1,3-cyclopentanedione.

Examples of a solvent include methanol, ethanol, propanol, isopropanol, butanol, isobutanol, and t-butanol as an alcohol solvent; diethyl ether, tetrahydrofuran, and dioxane as an ether solvent; benzene, toluene, and xylene as a hydrocarbon solvent; and water and supercritical $CO_2$ as an inorganic solvent. These can be used alone or in combination. An alcohol solvent or an inorganic solvent is preferred, and water is most preferred. The amount of the solvent to be used is, but is not limited to, preferably 0.1 part by weight or more and less than 1,000 parts by weight, most preferably 1 part by weight or more and less than 500 parts by weight, based on 1 part by weight of 1,3-cyclopentanedione. The reaction temperature is preferably from 25° C. to 150° C., most preferably from 40 to 120° C.

[The Second Step]

Next, a compound represented by the above formula (31) is etherified to produce an enone represented by the above formula (32).

In the above formula (32), $R^{50}$ represents a hydrogen atom or a linear or branched alkyl group, alkenyl group, or alkynyl group having 1 to 8 carbon atoms, and these groups may contain heteroatoms such as chlorine, bromine, nitrogen, oxygen, sulfur, iron, and cobalt. Specific examples of $R^{50}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. An alkyl group is preferred, and most preferred is a methyl group or an ethyl group. $R^{50}$ may be the same as $R^{49}$. In the above formula (32), the dotted line indicates that a bond may or may not be present. That is, the bond represents a triple bond or a double bond.

In the above formula (32), $R^{51}$ represents a linear, branched or cyclic alkyl group, alkenyl group, or alkynyl group having 1 to 8 carbon atoms. Specific examples of $R^{51}$ include a methyl group, an ethyl group, an n-propyl group, an isopropyl group, an n-butyl group, an isobutyl group, a t-butyl group, an n-pentyl group, an n-hexyl group, an n-heptyl group, an n-octyl group, a cyclohexyl group, and a benzyl group as an alkyl group; an allyl group and a methallyl group as an alkenyl group. An alkyl group is preferred, and most preferred is a methyl group or an ethyl group. $R^{50}$ and $R^{51}$ may be the same as each other.

The process of etherification of a compound represented by the above formula (31) is, but is not limited to, preferably a process of adding an alcohol having a corresponding substituent to a compound of the formula (31) in the presence of an acid catalyst, followed by heating the resulting mixture, in terms of safety and convenience.

The acid catalyst includes hydrogen chloride, sulfuric acid, and phosphoric acid as a mineral acid; p-toluenesulfonic acid as an organic acid; and titanium tetrachloride as a metal-based catalyst. Hydrogen chloride or sulfuric acid is preferred in terms of yield and cost. The amount of the acid catalyst is preferably from 0.01 to 10 times by mole based on a compound of the formula (13).

The amount of an alcohol ($R^{51}$—OH) having a corresponding substituent is preferably from 1 to 100 times by mole based on a compound of the formula (31).

The reaction temperature is preferably in the range of from 50° C. to 120° C., more preferably from 50 to 100° C., further preferably from 60° C. to 90° C., in terms of easiness in industrial implementation.

[The Third Step]

Furthermore, a malonic ester is added to an enone of the above formula (32) followed by decarboxylation to produce a compound represented by the above formula (33).

In the above formula (33), $R^{52}$ represents a hydrogen atom or a linear or branched alkyl group, alkenyl group, or alkynyl group having 1 to 8 carbon atoms, and these groups may contain heteroatoms such as chlorine, bromine, nitrogen, oxygen, sulfur, iron, and cobalt. Specific examples of $R^{52}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. An alkyl group is preferred, and most preferred is a methyl group or an ethyl group. $R^{52}$ may be the same as $R^5$. In the above formula (33), the dotted line indicates that a bond may or may not be present. That is, this indicates a triple bond or a double bond.

In the above formula (33), $R^{13}$ represents a linear, branched or cyclic alkyl group, alkenyl group, or alkynyl group having 1 to 8 carbon atoms. Specific examples of $R^{53}$ include a methyl group, an ethyl group, an n-propyl group, an isopropyl group, an n-butyl group, an isobutyl group, a t-butyl group, an n-pentyl group, an n-hexyl group, an n-heptyl group, an n-octyl group, a cyclohexyl group, and a benzyl group as an alkyl group; an allyl group and a methallyl group as an alkenyl group. An alkyl group is preferred, and most preferred is a methyl group or an ethyl group. $R^{52}$ and $R^{53}$ may be the same as each other.

This reaction is a reaction starting from the conjugate addition reaction of a malonic ester to an enone of the above formula (32), followed by elimination of an alkoxy group and decarboxylation. This reaction operation may be in accordance with a known process. For example, a simple process comprises allowing an alkoxide of an alkali metal to act on a malonic ester beforehand, drawing out an active hydrogen of the malonic ester to form an anion, and adding a compound of the above formula (32) thereto, followed by heating the resulting mixture.

The amount of the malonic ester to be used is preferably from 1 to 10 times by mole, most preferably from 1 to 5 times by mole, based on the enone. The amount of the alkali metal alkoxide to be used is, but is not limited to, preferably from 1 to 5 times by mole, most preferably from 1 to 2 times by mole, based on the malonic ester. Examples of alkali metal alkoxides include sodium methoxide, sodium ethoxide, potassium methoxide, potassium ethoxide, and potassium t-butoxide. Sodium methoxide is preferred.

The reaction temperature is preferably in the range of from 50° C. to 100° C., more preferably from 60° C. to 90° C., in terms of easiness in industrial implementation.

After the completion of the above reaction, the target compound of the formula (33) can be obtained by purification using a known process.

<A Tenth Invention>

A tenth aspect of the present invention is a process for producing a methylcyclopentenone represented by the above formula (35) characterized by decarboxylating a compound represented by the above formula (34).

The compound represented by the above formula (34) is a substance widely known as a raw material for jasmonates, and is a useful substance capable of easily obtaining jasmonates only by hydrogenating the double bond in the five-membered ring. That is, by using this compound as a starting material, the present invention can not only provide methylcyclopentenones useful as a jasmine fragrance and the like, but also can derivatively produce jasmonates which are also very useful as a jasmine fragrance and the like and have a large demand. In the fragrance industry, it is indispensable that many types of fragrance can be produced flexibly, and it is a great advantage in supply of raw materials and equipment and the like that a plurality of useful fragrances can be produced derivatively from the same starting material in this way. Moreover, the methylcyclopentenone of the above formula (35) not only has the skeleton of jasmine fragrances in itself, but also is useful as a precursor for obtaining a compound of the above formula (2) useful as a jasmine fragrance and the like. In addition, the compound of the above formula (35) can also be used as a precursor for the synthesis of prostaglandins and steroids.

In the above formula (34), $R^{54}$ represents a hydrogen atom or a linear or branched alkyl group, alkenyl group, or alkynyl group having 1 to 8 carbon atoms, and these groups may contain heteroatoms such as chlorine, bromine, nitrogen, oxygen, sulfur, iron, and cobalt. Specific examples of $R^{54}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. When the application to a jasmine fragrance is taken into consideration, a pentyl group is suitable, and a cis-2-pentenyl group, 2-pentynyl group, a 5-hydroxy-cis-2-pentenyl group, a 5-hydroxy-2-pentynyl group, and the like are also suitable.

In the above formula (34), $R^{55}$ represents a hydrogen atom or a linear, branched or cyclic alkyl group, alkenyl group, or alkynyl group having 1 to 8 carbon atoms. Specific examples of $R^{55}$ include a methyl group, an ethyl group, an n-propyl group, an isopropyl group, an n-butyl group, an isobutyl group, a t-butyl group, an n-pentyl group, an n-hexyl group, an n-heptyl group, an n-octyl group, a cyclohexyl group, and a benzyl group as an alkyl group; an allyl group and a methallyl group as an alkenyl group. An alkyl group is preferred, and most preferred is a methyl group or an ethyl group. $R^{54}$ and $R^{55}$ may be the same as each other.

In the above formula (35), $R^{56}$ represents a hydrogen atom or a linear or branched alkyl group, alkenyl group, or alkynyl group having 1 to 8 carbon atoms, and these groups may contain heteroatoms such as chlorine, bromine, nitrogen, oxygen, sulfur, iron, and cobalt. Specific examples of $R^{56}$ include a methyl group, an ethyl group, a butyl group, a pentyl group, a hexyl group, a heptyl group, an octyl group, and a nonyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. When the application to a jasmine fragrance is taken into consideration, a pentyl group is suitable, and a cis-2-pentenyl group, 2-pentynyl group, a 5-hydroxy-cis-2-pentenyl group, a 5-hydroxy-2-pentynyl group, and the like are also suitable. $R^{56}$ may be the same as $R^{54}$.

A known process may be used for the above decarboxylation. For example, when $R^{55}$ is a hydrogen atom, it can be achieved by using a general-purpose solvent such as methanol, ethanol, and tetrahydrofuran and heating the mixture in the presence of an acid or a base. Further, when $R^{55}$ is an alkyl group, it can be achieved by using dimethyl sulfoxide as a solvent and heating the mixture in the presence of sodium chloride.

The amount of an acid or a base is preferably from 0.01 to 20 times by mole, most preferably from 0.1 to 10 times by mole, based on the compound represented by the above formula (34).

The amount of a solvent is preferably 0.1 part by weight or more and less than 1,000 parts by weight, most preferably 1 part by weight or more and less than 500 parts by weight, based on 1 part by weight of the compound represented by the above formula (34). The reaction mixture is typically heated at 40° C. to 200° C., more preferably at 50° C. to 180° C.

After the completion of the above reaction, the target substituted cyclopentanone of the formula (35) can be obtained by purification using a known process.

<A Eleventh Invention>

A eleventh aspect of the present invention is a process for producing a γ-lactone represented by the above formula (39) which consists of the following two steps. By satisfying this requirement, the targeted γ-lactone can be produced safely and simply.

[1] The first step: a step of cleaving a furfuryl alcohol represented by the above formula (36) by hydrogen chloride in the presence of an alcohol represented by the above formula (37) to produce a γ-ketoester of the above formula (38); and

[2] The second step: a step of reducing a γ-ketoester represented by the above formula (38) to produce a γ-lactone represented by the above formula (39).

Each step is described below.

[The First Step]

First, a furfuryl alcohol represented by the above formula (36) is cleaved by hydrogen chloride in the presence of an alcohol represented by the above formula (37) to produce a γ-ketoester of the above formula (38). Specifically, it is produced by heating a reaction liquid containing a furfuryl alcohol represented by the above formula (36), an alcohol of the formula (37), and hydrogen chloride.

In the above formula (36), $R^{57}$ represents a hydrogen atom or a linear or branched alkyl group, alkenyl group, or alkynyl group having 1 to 12 carbon atoms, and these groups may contain heteroatoms such as chlorine, bromine, nitrogen, oxygen, sulfur, iron, and cobalt. Specific examples of $R^{57}$ include a methyl group, an ethyl group, a butyl group, a pentyl group, and a hexyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. When the application to a jasmine fragrance is taken into consideration, a pentyl group is suitable, and a cis-2-pentenyl group, 2-pentynyl group, a 5-hydroxy-cis-2-pentenyl group, a 5-hydroxy-2-pentynyl group, and the like are also suitable.

In the above formula (37), $R^{58}$ represents a hydrocarbon group having one or more carbon atoms. Specific examples of $R^{58}$ include a methyl group, an ethyl group, an n-propyl group, an isopropyl group, an n-butyl group, an isobutyl group, a t-butyl group, an n-pentyl group, an n-hexyl group, an n-heptyl group, an n-octyl group, a cyclohexyl group, and a benzyl group as an alkyl group; an allyl group and a methallyl group as an alkenyl group. When ease in distilling off, safety, cost, etc. in the treatment after reaction are taken into consideration, an alkyl group is preferred; and among others, an n-propyl group, an isopropyl group, an n-butyl group, an isobutyl group, and a t-butyl group are preferred, most preferably an n-butyl group and an isobutyl group.

In the above formula (38), $R^{59}$ represents a hydrogen atom or a linear or branched alkyl group, alkenyl group, or alkynyl group having 1 to 12 carbon atoms, and these groups may contain heteroatoms such as chlorine, bromine, nitrogen, oxygen, sulfur, iron, and cobalt. Specific examples of $R^{59}$ include a methyl group, an ethyl group, a butyl group, a pentyl group, a hexyl group, a heptyl group, an octyl group, and a nonyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. When the application to a jasmine fragrance is taken into consideration, a pentyl group is suitable, and a cis-2-pentenyl group, 2-pentynyl group, a 5-hydroxy-cis-2-pentenyl group, a 5-hydroxy-2-pentynyl group, and the like are also suitable. $R^{59}$ may be the same as $R^{57}$.

In the above formula (38), $R^{60}$ represents a linear, branched or cyclic alkyl group, alkenyl group, or alkynyl group having 1 to 8 carbon atoms. Specific examples of $R^{60}$ include a methyl group, an ethyl group, an n-propyl group, an isopropyl group, an n-butyl group, an isobutyl group, a t-butyl group, an n-pentyl group, an n-hexyl group, an n-heptyl group, an n-octyl group, a cyclohexyl group, and a benzyl group as an alkyl group; an allyl group and a methallyl group as an alkenyl group. An alkyl group is preferred, and most preferred is a methyl group or an ethyl group. $R^{60}$ may be the same as $R^{58}$, and $R^{59}$ and $R^{60}$ may be the same as each other.

A compound of the above formula (36) can be synthesized by a known process.

The alcohol represented by the above formula (37) is preferably used in an equimolar amount or more and in an amount of 100 times by mole or less, more preferably in an amount of 1.5 times by mole or more and 80 times by mole or less, based on a furfuryl alcohol represented by the formula (36).

In the reaction liquid used for the aforementioned production process, although other components, such as methanol, ethanol, ether, tetrahydrofuran, toluene, and xylene, may be present in addition to the alcohol of the formula (37), the percentage may be from about 0.01 wt % to 50 wt % of the reaction liquid.

The process of supplying hydrogen chloride into a reaction liquid includes a process of blowing hydrogen chloride gas; a process of adding hydrochloric acid (an aqueous solution of hydrogen chloride); and a process of adding an acyl chloride compound such as acetyl chloride and allowing it to react with an alcohol of the above formula (37) or the like, thereby generating hydrogen chloride in the reaction system; and the like. Among these, more desirable result is obtained in many cases when the process of blowing hydrogen chloride gas is taken.

Hydrogen chloride is used in an amount of from 0.01 mole to 5 moles based on 1.0 mole of a furfuryl alcohol of the above formula (36), more preferably from 0.01 mole to 2 moles.

The above heating temperature is from 30 to 150° C., more preferably from 40 to 120° C., most preferably from 50 to 100° C., when a practical reaction rate to be obtained is taken into consideration.

Furthermore, when a furfuryl alcohol of the above formula (36) is added dropwise to the mixture of an alcohol of the above formula (37) with hydrogen chloride, a γ-ketoester can be obtained in a high yield in many cases. In this case, a solution prepared by diluting the compound of the above formula (36) with the alcohol of the above formula (37) or other solvents, etc. beforehand may be added dropwise. Concentration of the solution is, for example, from 0.01 mol/l to 10 mol/l. The time of dropwise addition is, but is not limited to, preferably from 10 minutes to 5 hours, most preferably from 30 minutes to 3 hours.

After the completion of the above-mentioned reaction, the target γ-ketoester of the formula (38) can be obtained by performing purification in a known manner.

[The Second Step]

Next, a γ-ketoester represented by the above formula (38) is reduced to produce a γ-lactone of the above formula (39). Specifically, it can be achieved by reducing the ketone of γ-ketoester to form a hydroxyl group.

In the above formula (39), $R^{61}$ represents a hydrogen atom or a linear or branched alkyl group, alkenyl group, or alkynyl group having 1 to 12 carbon atoms, and these groups may contain heteroatoms such as chlorine, bromine, nitrogen, oxygen, sulfur, iron, and cobalt. Specific examples of $R^{61}$ include a methyl group, an ethyl group, a butyl group, a pentyl group, a hexyl group, a heptyl group, an octyl group, and a nonyl group as an alkyl group; a pentenyl group as an alkenyl group; and a pentynyl group as an alkynyl group. A pentenyl group includes a cis-2-pentenyl group and a 5-hydroxy-cis-2-pentenyl group, and a pentynyl group includes a 2-pentynyl group and a 5-hydroxy-2-pentynyl group. When the application to a jasmine fragrance is taken into consideration, a pentyl group is suitable, and a cis-2-pentenyl group, 2-pentynyl group, a 5-hydroxy-cis-2-pentenyl group, a 5-hydroxy-2-pentynyl group, and the like are also suitable. $R^{61}$ may be the same as $R^{59}$.

The process of reducing the ketone of a γ-ketoester represented by the above formula (38) may be in accordance with a known process. Examples of the process include a process in which a hydride such as sodium borohydride is used; and hydrogenation using a transition metal catalyst. Among others, the former is desirable due to the simplicity of operation. The amount of sodium borohydride is preferably from 0.25 to 10 times by mole, most preferably from 0.5 to 5 times by mole, based on the ketoester.

When the ketonic group of a γ-ketoester is reduced, a 4-hydroxy ester is produced, but at the same time a five-membered ring is formed very often to produce a γ-lactone. A known cyclization using an acid catalyst or the like may be applied when the five-membered-ring formation is imperfect.

For example, there may be added an acid catalyst in an amount of 0.01 to 10 times by mole based on the hydroxy ester and heated at 50 to 100° C. Examples of the acid catalyst include hydrogen chloride, sulfuric acid, and phosphoric acid as a mineral acid; p-toluenesulfonic acid as an organic acid; and titanium tetrachloride as a metal-based catalyst, and p-toluenesulfonic acid is preferred in terms of yield and cost.

By the way, it is known that an optically active γ-lactone has a great advantage in scent intensity and fragrance characteristics. If asymmetrical hydrogenation can be achieved in this process, great added value can be provided to a product. For asymmetrical hydrogenation, it is effective to use a transition metal catalyst having an asymmetric ligand and a biocatalyst such as baker's yeast, an enzyme, and the like. Thus, it is also one of the great features of the present invention that an optically active substance can be produced.

After the completion of the above reaction, the target γ-lactone of the formula (39) can be obtained by purification using a known process.

EXAMPLES

The present invention will be described in accordance with Examples.

The conditions in Examples are as follows:

Reaction vessel: use the one which is equipped with a magnetic stirrer, unless otherwise described;

Filtration of a catalyst: filtrate by pressure filtration using a film made from polytetrafluoroethylene;

Gas chromatograph:
Column: DB-1 (0.25 mm×30 m, a liquid phase film thickness of 0.25 μm) manufactured by J&W Scientific Company;
Column temperature: 100° C.×2 minutes to 250° C. (10° C./min)
Injection part temperature: 250° C.
Detection part temperature: 300° C.
Liquid chromatograph:
Column: Inertsil C4 manufactured by GL Science Inc.;
Developing solvent: 10 mM-$KH_2PO_4$, 1 mM-EDTA.2Na/$CH_3CN$=60/40;
Flow rate: 1.0 ml/min.

Examples 1 to 7

Comparative Examples 1 to 6

To a reactor (a volume of 50 ml) was respectively charged 1 g (4.5 mmol) of methyl (2-pentyl-3-keto-1-cyclopentenyl-)acetate (a compound in which $R^1$ represents an n-pentyl group and $R^2$ represents a methyl group in the above formula (1)) and 0.2 g of each catalyst shown in Table 1. Thereto were respectively added 10 ml of a solvent shown in Table 1, and the mixture was held at a temperature shown in Table 1. Pressure reduction and hydrogen introduction were repeated while stirring the mixture, and the air in the reactor was replaced with hydrogen at ordinary pressure. The mixture was continuously stirred in this state for 4 hours. Subsequently, the catalyst was removed from the reaction mixture by filtration, and then thereto were added 30 ml of water and 30 ml of toluene followed by stirring to extract a product into the toluene phase. Toluene was distilled off from this toluene phase, yielding methyl dihydrojasmonate (a compound in which $R^3$ represents an n-pentyl group and $R^4$ represents a methyl group in the above formula (2)). The yield and isomer ratio (cis-isomer/trans-isomer) of the resulting methyl dihydrojasmonate were determined by gas chromatography. The results are shown in Table 1.

reactor at a rate of 12 mL/min in this state, 42.0 g (0.21 mol) of methyl 4-oxodecanoate (a compound in which $R^5$ represents an n-pentyl group, and $R^6$ represents a methyl group in the above formula (3)) preliminarily dissolved in 1.5 L of dimethyl sulfoxide was added dropwise over 2 hours.

After completion of the dropwise addition, the pressure in the reactor was increased to about 15 mmHg; subsequently dimethyl sulfoxide was distilled off, and then the resulting reaction mixture was cooled to about 40° C. Thereto were added 1 L of water, 46 g of concentrated hydrochloric acid and 0.8 L of isobutyl alcohol. The resulting mixture was stirred and then allowed to stand, and the resulting organic phase was separated. Liquid chromatographic analysis of this organic phase showed that 2-n-pentyl-1,3-cyclopentanedione (a compound in which $R^7$ represents an n-pentyl group in the above formula (4)) was produced, and the yield was 92%.

Example 9

The air in a reactor (a volume of 5 L) was replaced with nitrogen gas at ordinary pressure, and 3.8 g (0.07 mol) of sodium methoxide and 0.5 L of dimethyl sulfoxide were charged to the reactor. The resulting solution was heated to 100° C., and 7.0 g (0.035 mol) of methyl 4-oxodecanoate (a compound in which $R^5$ represents an n-pentyl group, and $R^6$ represents a methyl group in the above formula (3)) preliminarily dissolved in 0.5 L of dimethyl sulfoxide was added dropwise at a rate of 8 ml/min with stirring. After completion of the dropwise addition, the reaction mixture was stirred for further 20 minutes under heating at the same temperature. The mixture was cooled to 25° C., and then thereto were added 100 g of water and 8.0 g of concentrated hydrochloric acid followed by stirring. Liquid chromatographic analysis of the reaction mixture showed that 2-n-pentyl-1,3-cyclopen-

TABLE 1

| | Catalyst | | Solvent | Temperature (° C.) | Yield (%) | isomer ratio (cis-isomer/trans-isomer) |
|---|---|---|---|---|---|---|
| Ex. 1 | Pd-carbon | (Pd content 10%) | formic acid | 25 | 94 | 75/25 |
| Ex. 2 | Pd-carbon | (Pd content 10%) | acetic acid | 25 | 95 | 78/22 |
| Ex. 3 | Pd-carbon | (Pd content 10%) | propionic acid | 25 | 94 | 78/22 |
| Ex. 4 | Pd-carbon | (Pd content 10%) | L-lactic acid (90% aqueous solution) | 25 | 96 | 88/12 |
| Ex. 5 | Pd-carbon | (Pd content 10%) | L-lactic acid (90% aqueous solution) | 0 | 95 | 92/8 |
| Ex. 6 | Pd-carbon | (Pd content 10%) | ethyl acetate | 25 | 88 | 58/42 |
| Ex. 7 | Rh-carbon | (Rh content 5%) | acetic acid | 25 | 89 | 70/30 |
| Comp. Ex. 1 | Pd-carbon | (Pd content 10%) | — | 25 | 48 | 44/56 |
| Comp. Ex. 2 | Pd-carbon | (Pd content 10%) | MeOH | 25 | 54 | 37/63 |
| Comp. Ex. 3 | Rh-carbon | (Rh content 5%) | MeOH [Note: 1] | 25 | 63 | 26/74 |
| Comp. Ex. 4 | Pd-carbon | (Pd content 10%) | EtOH | 25 | 28 | 39/61 |
| Comp. Ex. 5 | Pd-carbon | (Pd content 10%) | acetone | 25 | 15 | 46/54 |
| Comp. Ex. 6 | Pd-carbon | (Pd content 10%) | acetonitrile | 25 | 13 | 39/61 |

Note: 1)
Contains 35 mg of monosodium phosphate and 35 mg of dipotassium phosphate in 10 ml.

Example 8

The air in a reactor equipped with a three-blade stirrer (a volume of 5 L) was replaced with nitrogen gas at ordinary pressure, and 22.7 g (0.42 mol) of sodium methoxide and 3 L of dimethyl sulfoxide were charged to the reactor. The resulting solution was heated to about 90° C., and the inside of the reactor was decompressed to about 25 mmHg with stirring. While allowing dimethyl sulfoxide to be distilled off from the tanedione (a compound in which $R^7$ represents an n-pentyl group in the above formula (4)) was produced, and the yield was 86%.

Comparative Example 7

The air in a reactor (a volume of 2 L) was replaced with nitrogen gas at ordinary pressure, and 3.8 g (0.07 mol) of sodium methoxide and 0.5 L of xylene were charged to the reactor. The resulting solution was heated to 140° C., and while allowing xylene to be distilled off from the reactor at a rate of 8 mL/min, 7.0 g (0.035 mole) of methyl 4-oxodecanoate (a compound in which $R^5$ represents an n-pentyl group, and $R^6$ represents a methyl group in the above formula (3)) preliminarily dissolved in 0.5 L of xylene was added dropwise at a rate of 8 ml/min. After completion of the dropwise addition, the reaction mixture was heated and stirred for further 10 minutes while further allowing xylene to be distilled off. The mixture was cooled to 25° C., and thereto was added 100 g of water followed by stirring. The resulting mixture was then allowed to stand to separate the water phase. To the separated water phase were added 8.0 of concentrated hydrochloric acid and 100 ml of isobutyl alcohol followed by stirring. The resulting mixture was allowed to stand to separate the organic phase. Liquid chromatographic analysis of the organic phase showed that 2-n-pentyl-1,3-cyclopentanedione (a compound in which $R^7$ represents an n-pentyl group in the above formula (4)) was produced, and the yield was 29%.

Example 10

The air in a reactor (a volume of 2 L) was replaced with nitrogen gas at ordinary pressure, and 3.8 g (0.07 mol) of sodium methoxide and 0.8 L of dimethyl sulfoxide were charged to the reactor. The resulting solution was heated to about 107° C., and the inside of the reactor was decompressed to about 50 mmHg with stirring. While allowing dimethyl sulfoxide to be distilled off from the reactor at a rate of 14 mL/min in this state, 4.6 g (0.035 mol) of methyl levulinate (a compound in which $R^5$ represents a hydrogen atom, and $R^6$ represents a methyl group in the above formula (3)) preliminarily dissolved in 0.5 L of dimethyl sulfoxide was added dropwise at a rate of 8 ml/min.

After completion of the dropwise addition, the reaction mixture was heated and stirred for further 10 minutes while allowing dimethyl sulfoxide to be distilled off, and then cooled to 25° C. Thereto were added 200 g of water and 8.0 of concentrated hydrochloric acid followed by stirring. Liquid chromatographic analysis of the resulting reaction mixture showed that 1,3-cyclopentanedione (a compound in which $R^7$ represents a hydrogen atom in the above formula (4)) was produced, and the yield was 65%.

Comparative Example 8

The air in a reactor (a volume of 2 L) was replaced with nitrogen gas at ordinary pressure, and 3.8 g (0.07 mol) of sodium methoxide and 0.8 L of toluene were charged to the reactor. The resulting solution was heated to 110° C., and while allowing toluene to be distilled off from the reactor at a rate of 13 mL/min with stirring, 4.6 g (0.035 mol) of methyl levulinate (a compound in which $R^5$ represents a hydrogen atom, and $R^6$ represents a methyl group in the above formula (3)) preliminarily dissolved in 0.5 L of toluene was added dropwise at a rate of 7 ml/min. After completion of the dropwise addition, the reaction mixture was heated and stirred for further 10 minutes while allowing toluene to be distilled off. After distilling off toluene in vacuo, the resulting mixture was cooled to 25° C., and thereto were added 200 g of water and 8.0 of concentrated hydrochloric acid followed by stirring. Liquid chromatographic analysis of the resulting reaction mixture showed that 1,3-cyclopentanedione (a compound in which $R^7$ represents a hydrogen atom in the above formula (4)) was produced, and the yield was 7%.

Example 11

The air in a reactor (a volume of 2 L) was replaced with nitrogen gas at ordinary pressure, and 1.1 L of isobutanol containing 0.7 wt % of hydrogen chloride (prepared by preliminarily blowing hydrogen chloride therein) was charged to the reactor. The hydrogen chloride solution was heated to 80° C. and stirred, and then thereto was added dropwise 264 g (1.57 mol) of n-pentyl-furylcarbinol (a compound in which $R^8$ represents an n-pentyl group in the above formula (5)) over 3 hours. After completion of the dropwise addition, the mixture was stirred for further 10 minutes at the same temperature. Isobutanol was distilled off in vacuo, and the resulting mixture was cooled to 25° C. Gas chromatographic analysis of the liquid in the reactor showed that isobutyl 4-decanoate (a compound in which $R^{10}$ represents an n-pentyl group, and $R^{11}$ represents an isobutyl group in the above formula (7)) was produced, and the yield was 85%.

Example 12

The reaction was carried out in the same conditions as in Example 11 except that n-pentanol was used instead of isobutanol, yielding n-pentyl 4-decanoate (a compound in which both $R^{10}$ and $R^{11}$ represent an n-pentyl group in the above formula (7)) in 82% yield.

Comparative Example 9

The reaction was carried out under the same conditions as in Example 11 except that methanol was used instead of isobutanol and the reaction temperature was adjusted to 64° C. As a result, it was found that methyl 4-decanoate (a compound in which $R^{10}$ represents an n-pentyl group, and $R^{11}$ represents a methyl group in the above formula (7)) was produced, and the yield was 26%.

Comparative Example 10

The reaction was carried out under the same conditions as in Example 11 except that ethanol was used instead of isobutanol and the reaction temperature was adjusted to 78° C. As a result, it was found that ethyl 4-decanoate (a compound in which $R^{10}$ represents an n-pentyl group, and $R^{11}$ represents an ethyl group in the above formula (7)) was produced, and the yield was 31%.

Example 13

The air in a reactor (a volume of 2 L) was replaced with nitrogen gas at ordinary pressure, and 1.1 L of isobutanol containing 0.7 wt % of hydrogen chloride (prepared by preliminarily blowing hydrogen chloride therein) was charged to the reactor. The hydrogen chloride solution was heated to 80° C. and stirred, and then thereto was added dropwise 264 g (1.57 mol) of n-pentyl-furylcarbinol (a compound in which $R^{12}$ represents an n-pentyl group in the above formula (8)) over 3 hours. After completion of the dropwise addition, the mixture was stirred for further 10 minutes at the same temperature. Isobutanol was distilled off in vacuo, yielding isobutyl 4-oxodecanoate (a compound in which $R^{14}$ represents an n-pentyl group, and $R^{15}$ represents an isobutyl group in the above formula (10)). Gas chromatographic analysis showed that the yield of isobutyl 4-oxodecanoate was 86%.

To the resulting isobutyl 4-oxodecanoate were added 1 L of methanol and 250 g of 25% sodium hydroxide, and the mixture was stirred at 25° C. for 1 hour, followed by distilling off methanol in vacuo. Subsequently, thereto were added 2 L of water and 1 L of toluene. The resulting mixture was stirred at room temperature for 1 hour and then allowed to stand to separate the water phase. To the water phase were added 175 g of concentrated hydrochloric acid and 1.8 L of toluene. The resulting mixture was stirred for 10 minutes and then allowed to stand to separate the organic phase. Toluene in the organic phase was distilled off in vacuo and 1 L of toluene and 47.5 mL of concentrated sulfuric acid were added. The resulting mixture was heated under reflux for 1 hour and then cooled to 25° C. Thereto was gradually added 155 g of sodium hydrogencarbonate followed by stirring for 10 minutes at 25° C. Methanol was distilled off in vacuo and then 3 L of water and 1.8 L of toluene were added. The resulting mixture was stirred for 10 minutes at room temperature and then allowed to stand to separate the organic phase. Toluene in the organic phase was distilled off, yielding methyl 4-oxodecanoate (a compound in which $R^{17}$ represents an n-pentyl group, and $R^{18}$ represents a methyl group in the above formula (12)). Gas chromatographic analysis showed that the yield of methyl 4-oxodecanoate relative to isobutyl 4-oxodecanoate was 95%.

The air in a reactor (a volume of 5 L) was replaced with nitrogen gas at ordinary pressure, and 22.7 g (0.42 mol) of sodium methoxide and 3 L of dimethyl sulfoxide were charged to the reactor. The resulting solution was heated to about 90° C., and the inside of the reactor was decompressed to about 25 mmHg with stirring. While allowing dimethyl sulfoxide to be distilled off from the reactor at a rate of 12 mL/min in this state, 42.0 g (0.21 mol) of methyl 4-oxodecanoate preliminarily dissolved in 1.5 L of dimethyl sulfoxide was added dropwise at a rate of 12 ml/min.

After completion of the dropwise addition, the degree of decompression was increased to about 15 mmHg; dimethyl sulfoxide was distilled off at 81° C.; and then the resulting reaction mixture was cooled to about 40° C. Thereto were added 1 L of water, 46 g of concentrated hydrochloric acid and 0.8 L of isobutanol; and the resulting mixture was stirred and then allowed to stand to separate the organic phase. Isobutanol in the organic phase was distilled off in vacuo, yielding 2-n-pentyl-1,3-cyclopentanedione (a compound in which $R^{19}$ represents an n-pentyl group in the above formula (13)). Liquid chromatographic analysis showed that the yield of 2-n-pentyl-1,3-cyclopentanedione relative to methyl 4-oxodecanoate was 93%.

To 32.5 g (0.19 mol) of 2-n-pentyl-1,3-cyclopentanedione was added 650 ml of methanol containing 1 wt % of hydrogen chloride (prepared by preliminarily blowing hydrogen chloride therein), followed by heating under reflux for 5 hours and cooling to 25° C. Then, thereto was gradually added 15.4 g of sodium hydrogencarbonate followed by stirring for 30 minutes at 25° C. Methanol was distilled off in vacuo and then 200 mL of water and 200 mL of isobutanol were added. The resulting mixture was stirred for 10 minutes at 25° C. and then allowed to stand to separate the organic phase. Isobutanol in the organic phase was distilled off, yielding 2-pentyl-3-methoxy-2-cyclopentenone (a compound in which $R^{20}$ represents an n-pentyl group, and $R^{21}$ represents a methyl group in the above formula (14)). Gas chromatographic analysis showed that the yield of 2-pentyl-3-methoxy-2-cyclopentenone relative to 2-n-pentyl-1,3-cyclopentanedione was 80%.

The air in a reactor (a volume of 0.3 L) was preliminarily replaced with nitrogen at ordinary pressure. The reactor was charged with 13.5 g (70 mmol) of a 28% methanol solution of sodium methoxide and 140 ml of absolute methanol. Thereto was added 6.6 g (50 mmol) of dimethyl malonate, and the mixture was stirred for 30 minutes at 25° C. Thereto was added 6.6 g (36 mmol) of 2-pentyl-3-methoxy-2-cyclopentenone, and the mixture was heated under reflux for 24 hours in a nitrogen atmosphere. The resulting mixture was ice-cooled and neutralized by gradually adding 6.1 ml of concentrated hydrochloric acid, and methanol was distilled off. Thereto were added 50 ml of water and 100 ml of toluene, and then the mixture was stirred sufficiently and allowed to stand to separate the organic phase. The toluene in the organic phase was distilled off in vacuo followed by vacuum distillation, yielding methyl(2-pentyl-3-keto-1-cyclopentenyl-)acetate (a compound in which $R^{22}$ represents an n-pentyl group, and $R^{23}$ represents a methyl group in the above formula (15)). Gas chromatographic analysis showed that the yield of methyl(2-pentyl-3-keto-1-cyclopentenyl-)acetate relative to 2-pentyl-3-methoxy-2-cyclopentenone was 90%.

Comparative Example 11

To a solution of 32 g (0.24 mol) of anhydrous $AlCl_3$ in anhydrous nitromethane (30 ml) in a container having a volume of 0.1 L was added 12 g (0.1 mol) of 25° C. succinic acid in small quantities, and the mixture was stirred at 25° C. Highly corrosive HCl gas was generated violently, and the gas was removed with difficulty. In addition, since $AlCl_3$ is fuming (HCl gas), measures were taken against corrosion of equipment in the peripheral environment at the time of weighing, but it was with difficulty. Moreover, since nitromethane, which is a solvent, is explosive, it was handled while paying careful attention within explosion prevention equipment.

After charging succinic acid, the mixture was allowed stand to complete generation of HCl gas. Then, thereto was added 60 g (0.4 mol) of heptanoyl chloride, and the resulting mixture was heated at 80° C. for 8 hours. Since heptanoyl chloride is also fuming (HCl gas), measures were taken against corrosion of equipment in the peripheral environment at the time of weighing, but it was with difficulty. The mixture was cooled, poured onto 60 g of ice, and maintained at −10° C. for 10 hours, depositing a product as a solid. The product was subjected to suction filtration, washed with 10% NaCl water and toluene (20 ml×3 times), and dried, yielding 8.4 g (0.05 mol) of 2-pentyl-1,3-cyclopentanedione (a compound in which $R^1$ represents an n-pentyl group in the above formula (3)). Yields were 20.8%, 50.0%, and 12.5% relative to $AlCl_3$, succinic acid, and heptanoyl chloride, respectively. Simultaneously, wastewater containing a large amount of an aluminum-based and a chlorine-based compound was byproduced.

Example 14

In a reactor having a volume of 1.0 L, 10.0 g (0.10 mol) of 1,3-cyclopentanedione, 17.6 g (0.20 mol) of 1-pentene-3-ol and 1.0 g of p-toluenesulfonic acid were mixed with 500 ml of toluene, and the mixture was heated under reflux for 4 hours. During the reflux, byproduced water was azeotropically removed out of the system. Then, the mixture was mixed with a saturated water solution of sodium hydrogencarbonate and allowed to stand to separate the resulting organic phase. Toluene in the organic phase was distilled off in vacuo, yielding a compound in which $R^{32}$ represents an ethyl group in the above formula (21) (yield: 80%).

In 500 ml of xylene was dissolved 10.0 g of the compound, and the mixture was heated under reflux for 4 hours. Xylene was distilled off in vacuo, yielding a compound in which $R^{33}$ represents an ethyl group in the above formula (22) (yield: 85%).

In 100 ml of a non-aqueous methanol containing 1% of hydrogen chloride was dissolved 5.0 g of the compound, and the mixture was heated under reflux for 4 hours. Sodium hydrogencarbonate was added to the mixture to neutralize hydrogen chloride, and then methanol was distilled off in vacuo. Subsequently, thereto was added 50 ml of water and 250 ml of isobutanol, and then the mixture was allowed to stand to separate the organic phase. Isobutanol in the organic phase was distilled off in vacuo, yielding a compound in which $R^{34}$ represents an ethyl group, and $R^{35}$ represents a methyl group in the above formula (23) (yield: 86%).

In 5 ml of non-aqueous methanol was dissolved 1.0 g of the compound (non-aqueous methanol solution of the formula (23)). Next, 1.29 g of dimethyl malonate, 0.59 g of sodium methoxide, and 5 ml of non-aqueous methanol were mixed for 15 minutes at 25° C. The non-aqueous methanol solution of the formula (23) was added to the above solution, and the mixture was heated under reflux for 22 hours. Thereto was added 1 N hydrochloric acid and diethyl ether, followed by mixing and phase separation, and the organic phase was separated. The solvent in the organic phase was distilled off in vacuo, yielding a compound in which $R^{36}$ represents an ethyl group, and $R^{37}$ represents a methyl group in the above formula (24) (yield: 91%).

In 100 ml of dichloromethane was dissolved 1.0 g of the compound, and 1.08 g of m-chloroperbenzoic acid was added thereto under ice-cooling and then stirred at 25° C. for 4 hours. The mixture was mixed with 8 ml of 1 N sodium thiosulfate and 2 ml of a saturated aqueous solution of sodium hydrogencarbonate and allowed to stand to separate the resulting organic phase. The solvent in the organic phase was distilled off in vacuo, yielding a compound in which $R^{38}$ represents an ethyl group, and $R^{39}$ represents a methyl group in the above formula (25) (yield: 88%).

In the mixed solvent of 40 ml of tetrahydrofuran and 10 ml of water was dissolved 0.7 g of the compound, and then 1.1 g of 70% aqueous perchloric acid solution was added thereto and stirred at 25° C. for 1 hour. The mixture was neutralized with sodium hydrogencarbonate, and then tetrahydrofuran was distilled off in vacuo. Ethyl acetate was added thereto and then mixed, followed by allowing the mixture to stand, and the resulting organic phase was separated. Ethyl acetate in the organic phase was distilled off in vacuo, yielding a compound in which $R^{40}$ represents an ethyl group, and $R^{41}$ represents a methyl group in the above formula (26) (yield: 82%).

To a reactor were charged 0.5 g of the compound and 0.1 g of palladium-activated carbon (palladium content: 10%). Thereto was added 5 ml of ethyl acetate, and pressure reduction and hydrogen introduction were repeated with stirring to replace the air inside the reactor with hydrogen at ordinary pressure. In this state, the mixture was stirred for 6 hours. After removing the catalyst from the reaction mixture by filtration, ethyl acetate was distilled off in vacuo, yielding a compound in which $R^{42}$ represents ethyl and $R^{43}$ represents methyl in the above formula (27) (yield: 90%).

To 0.3 g of the compound were added 10 ml of methyl orthoformate and a catalytic amount of p-toluenesulfonic acid, and the mixture was heated under reflux for 1 hour. The mixture was neutralized with sodium hydrogencarbonate, and then methyl orthoformate was distilled off in vacuo. Subsequently, water and diethyl ether were added thereto and then mixed, followed by allowing the mixture to stand, and the resulting organic phase was separated. The solvent in the organic phase was distilled off in vacuo, yielding a compound in which $R^{44}$ represents ethyl, and $R^{45}$ represents methyl in the above formula (28) (yield: 95%).

In 5 ml of acetic anhydride was dissolved 0.2 g of the compound, and the mixture was added dropwise over 1 hour to 5 ml of acetic anhydride which was preliminarily heated under reflux. The mixture was heated under reflux for 20 minutes, and then acetic anhydride was distilled off in vacuo. To the mixture were added a saturated aqueous solution of sodium hydrogencarbonate and diethyl ether, followed by stirring the mixture and allowing it to stand, and the resulting organic phase was separated. The solvent of the organic phase was distilled off, yielding a 2,3-disubstituted cyclopentanone in which $R^{46}$ represents ethyl and $R^{47}$ represents methyl in the above formula (29) (yield: 88%). The ratio of the configuration of the substituents at 2- and 3-positions of the compound was as follows:

cis-isomer:trans-isomer=55:45.

Example 15

In a reactor with a volume of 0.1 L, 4.0 g of 1,3-cyclopentanedione, 6.0 g of potassium carbonate, and 6.6 g of 1-bromo-2-pentyne were added to 40 ml of water, and the mixture was heated at 60° C. for 6 hours. After adding 2 g of 5N sodium hydroxide and 30 ml of toluene followed by stirring at 25° C., the mixture was phase-separated and the aqueous phase was separated. Hydrochloric acid was added to the aqueous phase, and it was adjusted to pH=1. The aqueous phase was extracted twice with 50° C. toluene and the toluene was distilled off in vacuo, yielding a compound in which $R^{49}$ represents an ethyl group and a bond is present in the dotted line part in the above formula (31) (yield: 40%). In 20 ml of anhydrous methanol containing 1% of hydrogen chloride was dissolved 2.0 g of the compound, and the mixture was heated under reflux for 5 hours. After hydrogen chloride was neutralized with sodium hydrogencarbonate, methanol was distilled off in vacuo. After adding 20 ml of water and 20 ml of toluene, the mixture was phase-separated and the organic phase was separated. The toluene in the organic phase was distilled off in vacuo, yielding a compound in which $R^{50}$ represents an ethyl group and $R^{51}$ represents a methyl group in the above formula (32) (yield: 83%). A solution obtained by dissolving 1.0 g of the compound in 5 ml of anhydrous methanol was added to a solution obtained by stirring 1.33 g of dimethyl malonate, 0.61 g of sodium methoxide, and 5 ml of anhydrous methanol for 15 minutes at 25° C. beforehand, and the mixture was heated under reflux for 20 hours. Thereto was added 1N hydrochloric acid and diethyl ether followed by mixing, and the mixture was phase-separated and the organic phase was separated. The solvent in the organic phase was distilled off in vacuo, yielding a compound in which $R^{52}$ represents an ethyl group, $R^{53}$ represents a methyl group, and a bond is present in the dotted line part in the above formula (33) (yield: 89%).

Example 16

In a reactor with a volume of 10 ml, a mixture of 1 g (4.5 mmol) of methyl (2-pentyl-3-keto-1-cyclopentenyl-) acetate (a compound in which $R^{54}$ represents an n-pentyl group and $R^{55}$ represents a methyl group in the above formula (34)), 0.5 g (8.5 mmol) of sodium chloride, 0.2 g of water, and 3 ml of dimethyl sulfoxide was heated at 160° C. under nitrogen atmosphere for 3 hours. The mixture was cooled to 25° C., and then 10 ml of water and 20 ml of ethyl acetate were added thereto followed by stirring to thereby extract the product into the ethyl acetate phase. Gas chromatographic analysis showed that the yield of 2-n-pentyl-3-methyl-2-cyclopentenone was 82%.

Comparative Example 12

In a reactor with a volume of 0.1 L, 1 g of undecane-7,10-dione [$CH_3COCH_2CH_2COCH_2(CH_2)_4CH_3$], 7 ml of ethanol, and 25 ml of 0.5N sodium hydroxide were mixed, and the mixture was heated under reflux under nitrogen atmosphere for 5 hours. The mixture was cooled to 25° C., and then 20 ml of diethyl ether was added thereto followed by stirring to thereby extract the product into the diethyl ether phase. Gas chromatographic analysis showed that the yield of 2-n-pentyl-3-methyl-2-cyclopentenone was 52%.

Example 17

To the reactor (a volume of 2 L) in which the air was replaced with nitrogen gas at ordinary pressure, was charged 1.1 L of isobutanol containing 0.7 wt % of hydrogen chloride (prepared by preliminarily blowing hydrogen chloride therein). The hydrogen chloride solution was heated to 80° C. and stirred, and thereto was added dropwise 264 g (1.57 mol) of n-pentyl-furylcarbinol (a compound in which $R^{57}$ represents an n-pentyl group in the above formula (36)) over 3 hours.

After completion of the dropwise addition, the mixture was stirred for further 10 minutes at the same temperature. Isobutanol was distilled off in vacuo, yielding isobutyl 4-oxodecanoate (a compound in which $R^{59}$ represents an n-pentyl group, and $R^{60}$ represents an isobutyl group in the above formula (38)). Gas chromatographic analysis showed that the yield of isobutyl 4-oxodecanoate was 88%.

In 200 ml of 99.5% ethanol, was dissolved 24.2 g (0.10 mol) of isobutyl 4-oxodecanoate. Thereto was added 4.2 g (0.11 mol) of sodium borohydride in small quantities, and then the mixture was stirred for 10 minutes at 25° C. The solution was poured into 1 L of water, and 1 L of ethyl acetate was further added thereto followed by stirring to thereby extract the product into the ethyl acetate phase. Ethyl acetate was distilled off followed by vacuum distillation, yielding γ-decalactone (a compound in which $R^{61}$ represents an n-pentyl group in the above formula (39)). Gas chromatographic analysis showed that the yield of γ-decalactone relative to isobutyl 4-oxodecanoate was 93%. In the resulting γ-decalactone, a plastic-like flavor or acid taste was not observed at all, but it had a good peach-like aroma.

Comparative Example 13

To an autoclave (a volume of 1 L) was charged 349 g (3.0 mol) of n-heptanol and 0.06 g (0.27 mmol) of zinc bromide. The mixture was heated and stirred at 165° C. Into the mixture in this state was injected a mixed liquor of 57 g (0.66 mol) of methyl acrylate and 9.9 g (0.068 mol) of di-t-butylperoxide over 6 hours. The resulting mixture was stirred at the temperature for further 1 hour. Subsequently, unreacted n-heptanol was distilled off followed by vacuum distillation, yielding γ-decalactone. Gas chromatographic analysis showed that the yield of γ-decalactone was 69%. The resulting γ-decalactone was plastic-like in odor and acidulous, which indicated an inferior aroma.

INDUSTRIAL APPLICABILITY

The present invention makes it possible to provide a process for stereoselectively producing a cis-2,3-disubstituted cyclopentanone useful as a jasmine fragrance, an intermediate thereof or the like, and to provide a useful intermediate for producing the substituted cyclopentanone and a process for producing the intermediate.

BRIEF DESCRIPTION OF THE DRAWING

FIG. 1 is a diagram of the progress of enolization of a 2,3-disubstituted cyclopentanone under an acidic condition expected by a person skilled in the art.

TABLE 1

| | Catalyst | | Solvent | Temperature (° C.) | Yield (%) | isomer ratio (cis-isomer/trans-isomer) |
|---|---|---|---|---|---|---|
| Ex. 1 | Pd-carbon | (Pd content 10%) | formic acid | 25 | 94 | 75/25 |
| Ex. 2 | Pd-carbon | (Pd content 10%) | acetic acid | 25 | 95 | 78/22 |
| Ex. 3 | Pd-carbon | (Pd content 10%) | propionic acid | 25 | 94 | 78/22 |
| Ex. 4 | Pd-carbon | (Pd content 10%) | L-lactic acid (90% aqueous solution) | 25 | 96 | 88/12 |
| Ex. 5 | Pd-carbon | (Pd content 10%) | L-lactic acid (90% aqueous solution) | 0 | 95 | 92/8 |
| Ex. 6 | Pd-carbon | (Pd content 10%) | ethyl acetate | 25 | 88 | 58/42 |
| Ex. 7 | Rh-carbon | (Rh content 5%) | acetic acid | 25 | 89 | 70/30 |
| Comp. Ex. 1 | Pd-carbon | (Pd content 10%) | — | 25 | 48 | 44/56 |
| Comp. Ex. 2 | Pd-carbon | (Pd content 10%) | MeOH | 25 | 54 | 37/63 |
| Comp. Ex. 3 | Rh-carbon | (Rh content 5%) | MeOH [Note: 1] | 25 | 63 | 26/74 |
| Comp. Ex. 4 | Pd-carbon | (Pd content 10%) | EtOH | 25 | 28 | 39/61 |
| Comp. Ex. 5 | Pd-carbon | (Pd content 10%) | acetone | 25 | 15 | 46/54 |
| Comp. Ex. 6 | Pd-carbon | (Pd content 10%) | acetonitrile | 25 | 13 | 39/61 |

Note: 1)
Contains 35 mg of monosodium phosphate and 35 mg of dipotassium phosphate in 10 ml.

The invention claimed is:

1. A process for producing a substituted cyclopentanone represented by the formula (2):

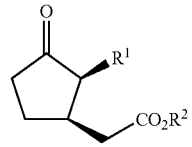

(2)

(wherein $R^1$ and $R^2$ represent a substituent having 1 to 8 carbon atoms and may be the same as each other) characterized by hydrogenating the double bond in the five-membered ring of a compound represented by the formula (1):

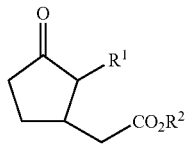 (1)

in the presence of a transition metal catalyst by using a carboxylic acid as a solvent.

2. The process for producing a substituted cyclopentanone according to claim 1, characterized in that the carboxylic acid is lactic acid.

3. The process for producing a substituted cyclopentanone according to claim 1, characterized in that a third component soluble in the solvent and affecting catalyst activity is not added.

4. The process for producing a substituted cyclopentanone according to claim 1, characterized in that the concentration of the carboxylic acid in the reaction solution at the start of hydrogenation is from 0.05 part by weight to 1,000 parts by weight based on one part by weight of the compound represented by the above formula (1).

5. The process for producing a substituted cyclopentanone according to claim 1, characterized in that the transition metal is palladium.

6. The process for producing a substituted cyclopentanone according to claim 1, characterized in that the transition metal catalyst is palladium-carbon.

* * * * *